United States Patent
Simmers

(10) Patent No.: US 9,789,299 B2
(45) Date of Patent: Oct. 17, 2017

(54) FORCE-CONTROLLED APPLICATOR FOR APPLYING A MICRONEEDLE DEVICE TO SKIN

(71) Applicant: 3M INNOVATIVE PROPERTIES COMPANY, St. Paul, MN (US)

(72) Inventor: Ryan P. Simmers, Fargo, ND (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/433,234

(22) PCT Filed: Nov. 14, 2013

(86) PCT No.: PCT/US2013/070115
§ 371 (c)(1),
(2) Date: Apr. 2, 2015

(87) PCT Pub. No.: WO2014/078545
PCT Pub. Date: May 22, 2014

(65) Prior Publication Data
US 2015/0246214 A1 Sep. 3, 2015

Related U.S. Application Data

(60) Provisional application No. 61/727,259, filed on Nov. 16, 2012.

(51) Int. Cl.
*A61M 37/00* (2006.01)

(52) U.S. Cl.
CPC . *A61M 37/0015* (2013.01); *A61M 2037/0023* (2013.01); *A61M 2037/0061* (2013.01)

(58) Field of Classification Search
CPC ...... A61M 37/0015; A61M 2037/0061; A61M 2037/0023; A61M 2037/0046
See application file for complete search history.

(56) References Cited

U.S. PATENT DOCUMENTS

| 4,472,480 A | 9/1984 | Olson |
| 4,584,355 A | 4/1986 | Blizzard |

(Continued)

FOREIGN PATENT DOCUMENTS

| WO | WO 02-30300 | 4/2002 |
| WO | WO 06/055802 | 5/2006 |

(Continued)

OTHER PUBLICATIONS

Daddona, "Parathyroid Hormone (1-34)-Coated Microneedle Patch System: Clinical Pharmacokinetics and Pharmacodynamics for Treatment of Osteoporosis"; Pharm Res, 2011, vol. 28, pp. 159-165.

(Continued)

*Primary Examiner* — Kevin C Sirmons
*Assistant Examiner* — Amber Stiles
(74) *Attorney, Agent, or Firm* — 3M Innovative Properties Company; Eric E. Silverman

(57) ABSTRACT

An applicator (100) for applying a microneedle device to a skin surface comprising a first portion (102) comprising a microneedle array (107), and a second portion (104) coupled to the first portion via a connector (106). The connector can be configured to yield or fracture by changing from a first state in which the connector is intact to a second state in which the connector is yielded or fractured when a threshold application force is applied to at least one of the first portion and the second portion in a direction substantially perpendicular with respect to the first portion. A method can include pressing the applicator in a direction substantially perpendicular to the first portion to press the microneedle array into the skin surface until the threshold application force is met or exceeded and the connector is changed to its second state.

17 Claims, 3 Drawing Sheets

(56) References Cited

U.S. PATENT DOCUMENTS

| | | | |
|---|---|---|---|
| 4,585,836 A | 4/1986 | Homan | |
| 4,591,622 A | 5/1986 | Blizzard | |
| 4,655,767 A | 4/1987 | Woodard | |
| 4,693,776 A | 9/1987 | Krampe | |
| 4,751,087 A | 6/1988 | Wick | |
| 4,834,979 A | 5/1989 | Gale | |
| 5,223,261 A | 6/1993 | Nelson | |
| 5,380,760 A | 1/1995 | Wendel | |
| 5,588,441 A | 12/1996 | Fishman | |
| 5,656,286 A | 8/1997 | Miranda | |
| 5,688,523 A | 11/1997 | Garbe | |
| 6,004,578 A | 12/1999 | Lee | |
| 6,024,976 A | 2/2000 | Miranda | |
| 6,091,975 A | 7/2000 | Daddona | |
| 6,149,935 A | 11/2000 | Chiang | |
| 6,312,612 B1 | 11/2001 | Sherman | |
| 6,365,178 B1 | 4/2002 | Venkateshwaran | |
| 6,379,324 B1 | 4/2002 | Gartstein | |
| 6,558,361 B1 | 5/2003 | Yeshurun | |
| 6,656,147 B1 * | 12/2003 | Gertsek | A61M 5/14248 604/185 |
| 6,855,131 B2 | 2/2005 | Trautman | |
| 7,648,484 B2 | 1/2010 | Yeshurun | |
| 2002/0091357 A1 * | 7/2002 | Trautman | A61B 17/205 604/117 |
| 2003/0054025 A1 | 3/2003 | Cantor | |
| 2004/0049150 A1 | 3/2004 | Dalton | |
| 2005/0261631 A1 | 11/2005 | Clarke | |
| 2006/0095061 A1 | 5/2006 | Trautman | |
| 2007/0185515 A1 | 8/2007 | Stout | |
| 2008/0009825 A1 | 1/2008 | Ringsred | |
| 2008/0108958 A1 | 5/2008 | Carter | |
| 2008/0114298 A1 * | 5/2008 | Cantor | A61M 37/0015 604/117 |
| 2008/0140049 A1 | 6/2008 | Kirby | |
| 2008/0183144 A1 | 7/2008 | Trautman | |
| 2008/0195035 A1 | 8/2008 | Frederickson | |
| 2009/0198189 A1 * | 8/2009 | Simons | A61M 37/0015 604/173 |
| 2011/0213335 A1 | 9/2011 | Burton | |
| 2011/0276027 A1 | 11/2011 | Trautman | |
| 2012/0123387 A1 | 5/2012 | Gonzalez | |

FOREIGN PATENT DOCUMENTS

| | | |
|---|---|---|
| WO | WO 2007-002522 | 1/2007 |
| WO | WO 2007-002523 | 1/2007 |
| WO | WO 2007-124411 | 11/2007 |
| WO | WO 2009-107806 | 9/2009 |
| WO | WO 2011-115602 | 9/2011 |
| WO | WO 2012-074576 | 6/2012 |
| WO | WO 2012-122162 | 9/2012 |
| WO | WO 2013-055638 | 4/2013 |
| WO | WO 2013-055641 | 4/2013 |
| WO | WO 2014-058746 | 4/2014 |

OTHER PUBLICATIONS

International Search Report for PCT International Application No. PCT/US2013/070115, mailed on Jan. 27, 2014, 6pgs.

* cited by examiner

FORCE-CONTROLLED APPLICATOR FOR APPLYING A MICRONEEDLE DEVICE TO SKIN

CROSS REFERENCE TO RELATED APPLICATIONS

This is a national stage filing under 35 U.S.C. §371 of PCT/US2013/070115, filed Nov. 14, 2013, which claims priority to U.S. Provisional Application No. 61/727,259, filed Nov. 16, 2012, the disclosure of which is incorporated herein by reference in its entirety.

FIELD

The present disclosure generally relates to applicators and methods for applying a microneedle device to skin to treat an area of the skin and/or deliver an active agent to the skin.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

In some cases, microneedle arrays can be used in conjunction with an applicator device capable of being used several times or as a single-use device. The microneedle arrays are generally used once and then discarded.

Issues related to applying microneedles include the ability to effectively and consistently insert the needles to a desired depth in the skin, as well as the ability to limit the maximum amount of application force that may be applied to a skin surface during treatment.

SUMMARY

The present disclosure relates to applicators that can be used to treat a selected site (e.g., on skin), and/or to apply an active ingredient to the treated site. One feature and advantage of applicators of the present disclosure is that they can achieve a desired depth of penetration (e.g., by achieving a minimum application force) and can limit the amount of force that can be applied to a microneedle array and to skin, for example, by causing the connection between two portions of the applicator to fracture when a threshold (e.g., maximum) application force has been met. Applicators of the present disclosure can be configured to deliver a range of forces (e.g., from a minimum required to achieve a desired depth of penetration to a maximum required to limit pain and/or depth of penetration) to achieve a desired depth of penetration range. In some embodiments, even if an outer portion of the applicator is continued to be pressed toward the skin, the microneedles of the applicator will not continue to be pressed into the skin after the maximum application force has been met.

In some embodiments, applicators of the present disclosure can be used to treat (e.g., perforate) skin with microneedles (e.g., uncoated microneedles) to create microchannels in the skin. Generally, targeted penetration of the microneedles includes penetration into the epidermis and dermis of the skin. In some embodiments, an active agent (e.g., a drug) can be coated on the microneedles, such that the active agent is delivered into the skin (e.g., into the epidermis and possibly the dermis) when the microneedles puncture the skin. In some embodiments, applicators of the present disclosure can be used to "pre-treat" skin with microneedles (e.g., coated or uncoated) for subsequent application of an active over the treated site. The active agent can be applied by applying a transdermal patch comprising the active agent over the treated site, or in some embodiments, a lotion, cream, gel, ointment, or the like, can be applied over the treated site. Still, in some embodiments, an active agent can be applied topically to skin (e.g., in the form of a lotion, cream, gel, ointment, or the like), and the applicator can be used to apply the microneedles (e.g., uncoated or coated) to the skin after topical application of the active agent. Furthermore, in some embodiments, the portion of the application comprising the microneedle array can be left on the skin for a treatment period. In some embodiments in which the microneedles are left to penetrate the skin for a treatment period, the microneedles can be solid or hollow. In the case of hollow microneedles, the microneedles can be used to continuously infuse an active agent into the epidermis and/or dermis for a desired treatment period. In some embodiments, a combination of any of the above application or treatment techniques can be performed using applicators of the present disclosure.

Some aspects of the present disclosure provide an applicator for applying a microneedle array to a skin surface. The applicator can include a first portion comprising a microneedle array and defining a first major surface from which the microneedle array protrudes, the first major surface configured to be substantially parallel with the skin surface and configured to be positioned toward the skin surface. The applicator can further include a second portion coupled to the first portion via a connector. The connector can be configured to yield or fracture by changing from a first state in which the connector is intact to a second state in which the connector is yielded or fractured when an application force is applied to at least one of the first portion and the second portion in a direction substantially perpendicular with respect to the first major surface of the first portion that meets or exceeds a threshold application force. The second portion can define a second major surface which configured to be positioned toward the skin surface. At least a portion of the microneedle array can extend beyond the first major surface and the second major surface when the connector is in the first state.

Some aspects of the present disclosure provide a method of applying a microneedle array to a skin surface. The method can include providing the above-described applicator, and pressing the applicator in a direction substantially perpendicular to the first major surface to press the microneedle array into the skin surface until the threshold application force is met or exceeded and the connector is changed to its second state.

Other features and aspects of the present disclosure will become apparent by consideration of the detailed description and accompanying drawings.

DETAILED DESCRIPTION

Figure 1:
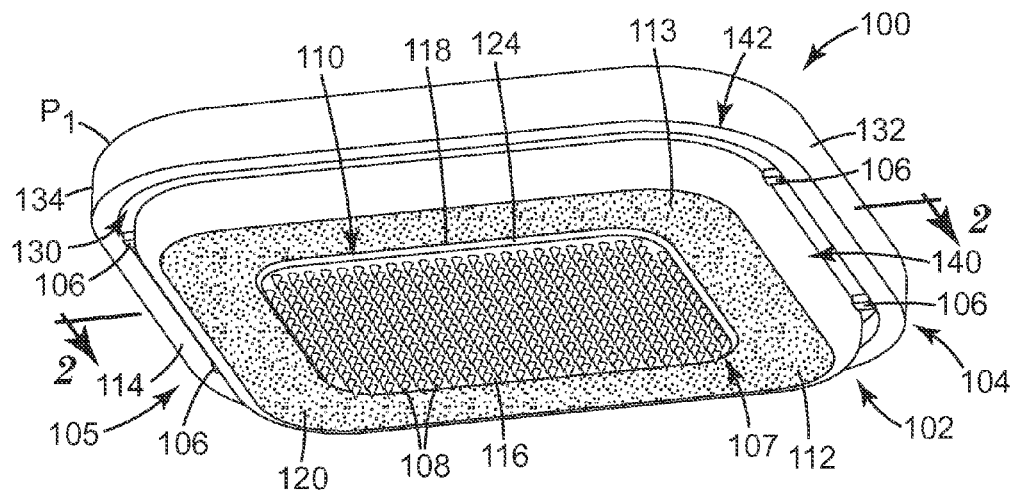
FIG. 1 is a bottom perspective view of an applicator according to one embodiment of the present disclosure, the applicator shown unactuated and comprising a first portion comprising a microneedle array; a second portion; and a connector, shown in a first state, coupling the first portion and the second portion; the second portion shown in a first position relative to the first portion.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "top," "bottom," "upper," "lower," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an applicator and method for applying a microneedle device, comprising an array of microneedles, to skin (or a biological membrane) to treat the skin (i.e., create small holes or perforations or micropores in the skin) and/or to deliver an active agent to the skin. Particularly, applicators of the present disclosure can be configured such that a portion of the applicator that is leveraged to press the microneedles into the skin suddenly loses its leverage after a threshold (e.g., maximum) application force has the met. By way of example, in some embodiments, the applicator can include more than one portion, and the portion a user would press on to press the microneedles into a skin surface can be coupled to (e.g., directly or indirectly) a portion of the applicator comprising the microneedles by a connector having a strength (e.g., tensile strength, shear strength, yield strength, etc., depending on the configuration of the applicator and the connection) that is equal to or less than the threshold application force. As a result, when the threshold application force is met or exceeded, the connector will yield or fracture, causing the portion of the applicator a user is pressing on to no longer be able to be leveraged to press the microneedles into the skin. The skin-contacting surface of the applicator can include an adhesive to hold the applicator (or a portion of the applicator comprising the microneedle array) in place on the skin during the desired treatment and/or delivery period, and the applicator (or portion thereof) can be removed when desired, e.g., when the desired treatment and/or delivery period has expired.

A "threshold application force" generally refers to the force required to achieve a desired depth of penetration (e.g., average depth of penetration).

The term "fracture" is used to refer to when the connector is broken, separated, torn, and/or sheared by meeting or exceeding the connector's ultimate strength (e.g., ultimate tensile strength, ultimate shear strength, etc.). The term "yield" is used to refer to when the connector may not entirely separate or break but is plastically deformed by meeting or exceeding the connector's yield point, to an extent where the connector no longer holds other elements in the same relative position.

In some existing cases, a mechanical device or tool can be used to treat skin with microneedles at a precisely-controlled velocity and to a precisely-controlled depth of penetration (e.g., average depth of penetration). However, the applicators of the present disclosure can allow microneedles to be applied by hand (i.e., manual pressure, without requiring an additional mechanical device or tool) in a force-controlled manner. As a result, even inexperienced users applying the applicators of the present disclosure by hand will be inhibited from applying too great of an application force to the skin with the microneedle array, because at least a portion of the applicator will yield or fracture when the threshold application force (and, accordingly, the desired depth of penetration) is achieved. In addition, some existing microneedle applicators require the use of a stored energy element, such as a spring, to accelerate a microneedle array into the skin and achieve a desired actuation velocity. On the contrary, the applicators of the present disclosure do not require the use of any stored energy element. For at least these reasons, the applicators of the present disclosure therefore provide a simple, low-cost and robust solution for applying microneedles to skin (e.g., using hand pressure) while controlling the depth of penetration (e.g., an average depth of penetration) and the maximum application force.

Some existing applicators require a specific application velocity of the microneedles to puncture skin. With applicators of the present disclosure, generally a gentle hand pressure is sufficient to achieve the desired depth of penetration, while also limiting the maximum application force that can be applied with the microneedles.

As mentioned above, applicators of the present disclosure may be useful when applied to the skin as a "pretreatment" step, that is, when applied to the skin to disrupt the stratum corneum layer of skin and then removed. The disrupted area of skin may then be useful for allowing enhanced delivery of a topical composition (e.g., a solution, a cream, a lotion, a gel, an ointment, or the like) or patch comprising an active agent that is applied to the disrupted area. Applicators of the present disclosure may also be useful when the microneedles are provided with a dried coating comprising an active agent that dissolved from the microneedles after they are inserted into the skin. As a result, applicators of the present disclosure may have utility for enhancing delivery of molecules to the skin, such as in dermatological treatments, vaccine delivery, or in enhancing immune response of vaccine adjuvants. As mentioned above, in some embodiments, the active agent may be applied to the skin (e.g., in the form of a solution that is swabbed onto the skin surface, or as a cream, lotion, gel, ointment, or the like, that is rubbed into the skin surface) prior to applying the microneedles of the applicators of the present disclosure.

When a patch is applied to the treated or disrupted site, the patch can be provided in a variety of forms and can include a drug reservoir comprising an active agent for delivery to the treated site. Any transdermal patch suitable for the continuous transdermal delivery of a therapeutically effective amount of an appropriate medicament may be used. Suitable transdermal patches include gelled or liquid reservoirs, such as in U.S. Pat. No. 4,834,979 (Gale), so-called "reservoir" patches; patches containing matrix reservoirs attached to the skin by an adjacent adhesive layer, such as in U.S. Pat. No. 6,004,578 (Lee et al.), so-called "matrix" patches; and patches containing pressure-sensitive adhesive (PSA) reservoirs, such as in U.S. Pat. No. 6,365,178 (Venkateshwaran et al.), U.S. Pat. No. 6,024,976 (Miranda et al.), U.S. Pat. No. 4,751,087 (Wick) and U.S. Pat. No. 6,149,935 (Chiang et al.), so-called "drug-in-adhesive" patches, the disclosures of which are hereby incorporated by reference. In some embodiments, the drug reservoir can be provided in the form of a matrix layer containing drug, the matrix layer being adhered to a skin-contact adhesive of the patch. Such a matrix may be an adhesive layer. Alternatively the matrix layer may be non-adhesive or weakly adhesive and rely upon the surrounding rim of skin-contact adhesive on an adhesive patch to secure the patch in place and keep the drug reservoir in contact with the skin surface.

In another embodiment, the drug reservoir can be provided in the form of solid particles embedded on the surface or within the skin-contact adhesive of the patch. In particular, these particles may be hydrophilic, so that contact with aqueous fluid exposed at the surface of the treated skin will cause them to dissolve or disintegrate, thus releasing drug into the skin.

In another embodiment, the drug reservoir can be provided within the skin-contact adhesive of the patch. The drug may be mixed with the skin-contact adhesive prior to forming the patch or it may be applied to the skin-contact adhesive of the patch in a separate process step. Examples of suitable methods for applying drug to an adhesive layer may be found in U.S. Patent Application Publication No. 2003/054025 (Cantor et al.) and U.S. Pat. No. 5,688,523 (Garbe et al.), the disclosures of which are hereby incorporated by reference.

The length of time between (i) treatment of the skin with microneedles to increase permeability and (ii) placement of the active agent in contact with the treated skin area may vary. In one embodiment, this length of time can be kept to a minimum in order to avoid any possibility of the skin barrier reforming through a healing process. The minimum length of time can be generally governed by the time it takes to remove the applicators of the present disclosure from the skin and apply the active agent, for example, by swabbing on a solution, rubbing in a cream or lotion, remove the liner of a patch and applying its adhesive over the treated site (e.g., if a patch is being employed), etc. This time may be less than about 1 minute, less than about 30 seconds, less than about 10 seconds, or less than about 5 seconds. There is no reason, however, that this time cannot be extended to many minutes or hours if so desired. It is generally known that the length of time that the skin will remain increasingly permeable after treatment depends on the type of treatment and whether the skin is occluded or not after treatment. In some instances, increased permeability can be maintained for up to several days as long as the treated site remains occluded and even in the absence of occlusion the skin may have increased permeability for up to several hours. Thus, if it presented some convenience or clinical benefit, one could treat the site and delay drug delivery by wearing some type of dressing over the treated site until such time as one desired to begin drug delivery, at which time the active agent could be applied to the treated skin.

In discussing the applicators of the present disclosure, the term "downward," and variations thereof, is sometimes used to describe the direction in which microneedles are pressed into skin, and "upward" to describe the opposite direction. However, those of skill in the art will understand that the applicators can be used where the microneedles are pressed into skin at an angle to the direction of the earth's gravity, or even in a direction contrary to that of the earth's gravity, and these terms are only used for simplicity and clarity to describe relative directions.

Figure 2A:
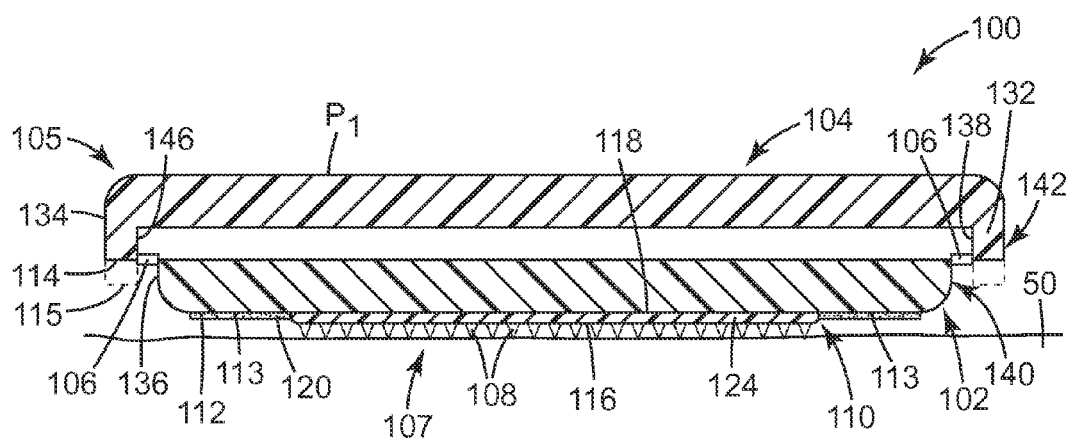
FIG. 2A is a side cross-sectional view of the applicator of FIG. 1, taken along like 2-2 of FIG. 1, the applicator shown as it is being applied to a skin surface, with the second portion in the first position, the connector in its first state, and the microneedles of the microneedle array penetrating the skin.
Figure 2B:
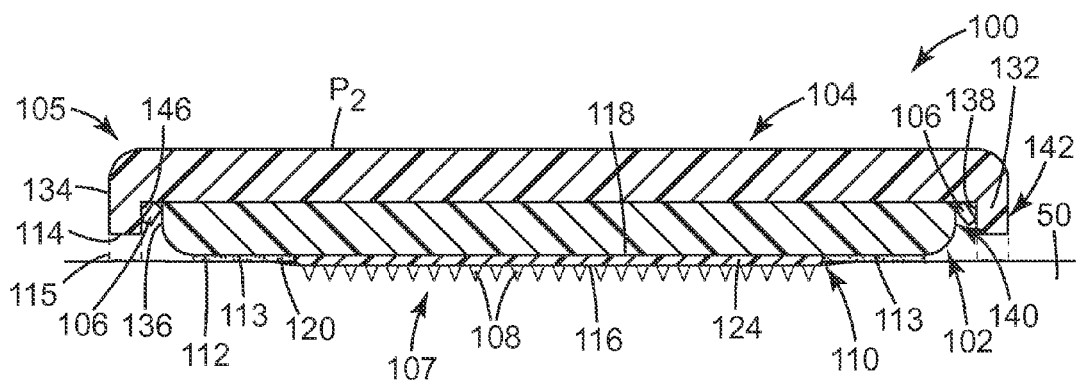
FIG. 2B is a side cross-sectional view of the applicator of FIGS. 1 and 2A, taken along line 2-2 of FIG. 1, with the second portion in a second position relative to the first portion and the connector in a second state.
Figure 2C:
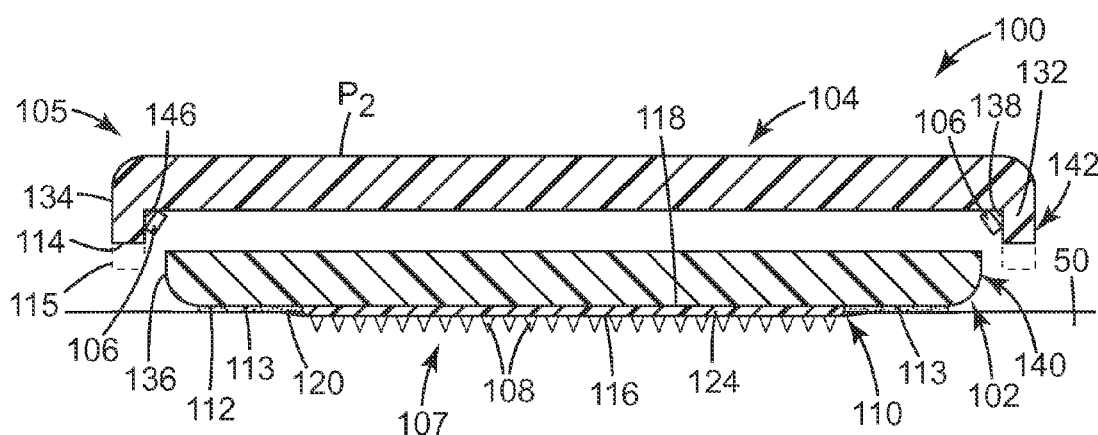
FIG. 2C is a is a side cross-sectional view of the applicator of FIGS. 1, 2A and 2B, taken along line 2-2 of FIG. 1, with the second portion being removed from the first portion and the microneedles of the microneedle array still penetrating the skin.

FIGS. 1-2C illustrate an applicator 100 according to one embodiment of the present disclosure. The applicator 100 includes a first portion 102 and a second portion 104 coupled to the first portion 102 via one or more connectors 106 (four connectors 106 are shown by way of example only). As mentioned above, in some embodiments, the connector(s) 106 can be frangible and can break, fracture or shatter when a threshold application force is reached, and in some embodiments, at least a portion of the connector(s) 106 can yield or plastically deform when a threshold application force is reached. In some embodiments, the connector 106 is one continuous section of material, and in some embodiments, the applicator 100 includes a plurality of connectors 106. For simplicity, one connector 106 will be described, but it should be understood that the same description can apply to a plurality of connectors 106. In some embodiments, the first portion 102 and the second portion 104 can be referred to as forming relative portions of a body or housing 105. Furthermore, in some embodiments, the first portion 102, the second portion 104 and the one or more connectors 106 can be integrally formed.

In some embodiments, the connector 106 can also provide audible and/or tactile feedback to a user when the threshold application force has been achieved to indicate to a user that the threshold application force has been achieved and hand pressure on the applicator 100 can be discontinued. For example, in embodiments in which the connector 106 fractures, audible feedback can include a snapping or clicking sound from the connector 106 breaking. In some embodiments, the connector 106 can also provide tactile feedback to a user, for example, when the second portion 104 loses resistance or 'gives way.'

As shown, the first portion 102 includes a microneedle array 107 comprising microneedles 108. The first portion 102 further includes or defines a first major surface 112 from which the microneedle array 107 protrudes. In some embodiments, the microneedles 108 can be configured to treat skin (i.e., create small holes or perforations or micropores in the skin) and/or deliver an active agent via skin, particularly, mammalian skin, and particularly, transdermally. Various microneedles that can be employed in applicators and methods of the present disclosure are described in greater detail below.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The "microneedle array" 107 can form a portion of a "microneedle device" or a "microneedle array assembly" 110 and can include the array 107 of microneedles 108 (or, collectively, the "microneedle array" 107) and any supporting structure or substrate used to support the microneedle array 107 and/or to couple the microneedle array 107 to other structures or components of the applicator 100. For example, in some embodiments, the "microneedle device" or "microneedle array assembly" 110 can refer to the microneedle array 107, and a carrier (or "array carrier" or "substrate") 124. In the embodiment illustrated in FIGS. 1-2C, the microneedles 108 are formed in or directly coupled to the carrier 124. However, it should be understood that additional layers can be coupled between the illustrated carrier 124 and the microneedle array 107. For example, in some embodiments, the microneedle array 107 can be formed in or directly coupled to a first carrier layer that is then coupled to the layer referenced in FIGS. 1-2C by numeral 124. Other suitable configurations are also possible.

The microneedle device 110 (or the carrier 124) can include a first side 116 comprising the microneedle array 107 and a second side 118 opposite the first side 116. The first side 116 can be positioned to face the skin surface 50. The microneedles 108 can be coupled to, or formed with, the first side 116, such that the microneedle device 110 is (and particularly, the microneedles 108 are) positioned to face the skin surface 50.

In some embodiments, the microneedle array 107 can be coupled to the carrier 124 (e.g., if provided by an additional layer that is then coupled to the carrier 124) by a variety of coupling means, including, but not limited to, press-fit or friction-fit engagement, snap-fit engagement, magnets, hook-and-loop fasteners, adhesives, cohesives, clamps, heat sealing, stitches, staples, screws, nails, rivets, brads, crimps, welding (e.g., sonic (e.g., ultrasonic) and/or thermal welding), any thermal bonding technique (e.g., heat and/or pressure applied to one or both of the components to be coupled), other suitable coupling means, or combinations thereof. Alternatively, as shown in FIGS. 1-2C, in some embodiments, the carrier 124 and the microneedle array 107 can be integrally formed.

The carrier 124 (e.g., the second side 118) can also be coupled to the first major surface 112 of the first portion 102 by any of the above-described coupling means. Alternatively, the microneedle array 107 can simply be integrally formed with the first major surface 112 of the first portion 102.

As shown, generally, the first portion 102 is the portion of the applicator 100 located toward the skin surface 50 relative to the second portion 104 when the applicator 100 is in use. In some embodiments, the first major surface 112 can include one or more non-treatment (or non-structured) regions or areas 113 adjacent the microneedle array 107 without microneedles 108. In some embodiments, such non-treatment areas surround the microneedle array 107 on all sides.

In some embodiments, the first portion 102 can be configured such that the non-treatment region(s) 113 of the first major surface 112 also come into contact with the skin 50, e.g., after the microneedles 108 have been fully inserted into the skin 50. As a result, in some embodiments, as shown in FIGS. 1-2C, the first major surface 112 (and, particularly, the non-treatment region(s) 113 thereof) can include a skin-contact adhesive 120 (described in greater detail below) and the first portion 102 can remain coupled to the skin 50 for a desired treatment and/or delivery period after the connector 106 yields or fractures, and optionally, after the second portion 104 has been removed from the skin 50.

As a result of the non-treatment region(s) 113 and the skin-contact adhesive 120, in some embodiments, the first portion 102 of the applicator 100 can function as a patch, even though the "patch" may be more rigid than other known patches. The microneedles 108 can be arranged in any desired pattern or distributed over the first major surface 112 randomly. As shown, the microneedles 108 can be arranged in uniformly spaced rows. When arranged in rows, the rows can be arranged so that the microneedles 108 are aligned or offset. In some embodiments (not shown), the microneedles 108 can be arranged in a polygonal pattern such as a triangle, square, rectangle, pentagon, hexagon, heptagon, octagon, or trapezoid. In other embodiments (not shown), the microneedles 108 can be arranged in a circular or oval pattern.

In some embodiments, the surface area of the first major surface 112 covered with microneedles 108 is about 0.1 $cm^2$ to about 20 $cm^2$. In some of these embodiments, the surface area of the first major surface 112 covered with microneedles 108 is about 0.5 $cm^2$ to about 5 $cm^2$. In some other of these embodiments, the surface area of the first major surface 112 covered with microneedles 108 is about 1 $cm^2$ to about 3 $cm^2$. In still other of these embodiments, the surface area of the first major surface 112 covered with microneedles 108 is about 1 $cm^2$ to about 2 $cm^2$.

In some embodiments, the non-treatment region(s) can have a collective area of more than about 1 percent and less than about 75 percent of the total area of the first major surface 112 that faces the skin surface 50. In another of these embodiments, the non-treatment region(s) can have a collective area of more than about 0.65 $cm^2$ (0.10 square inch) to less than about 6.5 $cm^2$ (1 square inch).

The housing or body 105 (i.e., the first portion 102 and the second portion 104) as well as any layers making up the microneedle device 110 in addition to the microneedles 108 themselves (e.g., the carrier 124) can be formed of a variety of materials, including but not limited to, thermoset plastics (e.g., acetal resin available under the trade designation DELRIN® DuPont Corporation, Wilmington, Del.; other suitable thermoset plastics, or combinations thereof), thermoformable plastics (e.g., polyethylene, polypropylene, other suitable thermoformable plastics, or combinations thereof), or metals (e.g., stainless steel, aluminum, other suitable metals, or combinations thereof), or combinations thereof.

As shown, the second portion 104 can include or define a second major surface 114. The first major surface 112 and the second major surface 114 are generally configured to be substantially parallel with a skin surface 50 to which the applicator 100 will be applied, and are generally configured to be positioned toward, or facing, the skin surface 50. As the applicator 100 is applied to the skin surface 50, the applicator 100 can be held in an orientation in which the first major surface 112 of the first portion 102 is generally parallel with the skin surface 50. Such an orientation can be desirable, particularly in embodiments in which the microneedles 108 are oriented generally perpendicularly with respect to the skin surface 50. Parallel alignment of the applicator 100 thus allows for the microneedles 108 to be pressed straight downward into the skin 50, thus minimizing the chance of bending the microneedles 108 and allowing for reproducible penetration of the microneedles 108 of the array 107 to a desired depth (e.g., average depth) in the skin 50. By "substantially parallel," it should be understood that the skin 50 is a biological surface and as such has some natural roughness and irregularity. Thus, variations in alignment of the applicator 100 with respect to parallel having a magnitude similar to that of the natural roughness of the skin surface 50 are considered to be substantially parallel.

The connector 106 is generally configured to yield or fracture when an application force is applied to at least one of the first portion 102 and the second portion 104 in a direction substantially perpendicular with respect to the first major surface 112 of the first portion 102 that meets or exceeds a threshold application force. As a result, the connector 106 can be designed to limit the amount of force at which the microneedles 108 can be inserted into the skin 50. As described above, this can also limit the depth to which the microneedles 108 can penetrate the skin 50. When the applicator 100 is pressed into the skin 50, i.e., generally in a direction perpendicular to the first major surface 112 (and the second major surface 114) to cause the microneedles 108 to puncture or perforate the skin 50, the connector will yield or fracture when that maximum application force is reached.

As a result, the connector 106 has:
(i) an first (or unfractured or unyielded) state in which the connector 106 is intact, the first portion 102 and the second portion 104 are coupled together, and the applicator 100 is configured to press the microneedle array 107 into the skin surface 50 to a desired depth and force, and
(ii) a second (or fractured or yielded) state in which the connector 106 is fractured or yielded, and the first portion 102 and the second portion 104 are either no longer coupled together (i.e., separated, e.g., in the case of the connector 106 fracturing) or have lost the mechanical connection or structural integrity that results in force applied to one of the first portion 102 and the second portion 104 necessarily being transferred to the other.

For example, in some embodiments, it could be conceivable that the connector 106 is merely plastically deformed to an extent that pressure on the second portion 104 toward the skin surface 50 no longer exerts any force on the first portion 102 and the microneedle array 107, particularly, when the second portion 104 is configured to surround, envelope and/or receive at least a portion of the first portion 102, such that the second major surface 114 abuts the skin surface 50 after the connector 106 fractures or yields, changing the connector 106 to its second state.

As described in greater detail below, in some embodiments, the applicator 100 can be configured such that when the connector 106 is in its second state, the microneedle array 107 can no longer be pressed into the skin 50 via the second portion 104.

FIGS. 1 and 2A show the applicator 100 in a first (or primed, or unactuated, or treatment) state. FIG. 2A also shows the applicator 100 as it is about to be applied to skin, or a skin surface, 50. FIG. 2B shows the applicator 100 after the microneedles 108 have punctured the skin 50 and the threshold application force has been met, i.e., with the applicator 100 in a second, or actuated, state. FIG. 2C shows the applicator 100 with the second portion 104 being removed, while the first portion 102 comprising the microneedles 108 of the applicator is left on the skin 50.

The applicators 100 of the present disclosure are configured to be pressed as a whole (e.g., by pressing on the second portion 104) in a direction substantially perpendicular to the first major surface 112 (and, optionally, the second major surface 114) to press the microneedle array 107 into the skin surface 50 (e.g., to within a specified range of depths under a specified range of forces) until the threshold application force is reached and the connector 106 yields or fractures.

The phrase "directed substantially perpendicularly with respect to the first major surface" or "in a direction oriented substantially perpendicularly with respect to the first major surface," or variations thereof, generally refers to a motion that is directed generally perpendicularly or normal to the first major surface 112. In some embodiments, the first major surface 112 can have some curvature or undulations. In such embodiments, a direction that is "perpendicular with respect to the first major surface 112" would generally refer to a direction that is normal to a tangent of such a curved or arcuate surface.

In some embodiments, the threshold application force can be at least 0.8 lbf (3.5 N), in some embodiments, at least 1 lbf (4.4 N), in some embodiments, at least 3 lbf (13.3 N), and in some embodiments, at least 5 lbf (22.2 N). In some embodiments, the threshold application force can be no greater than 10 lbf (44.5 N), in some embodiments, no greater than 5 lbf (22.2 N), and in some embodiments, no greater than 2 lbf (8.9 N).

By controlling the application force that can be applied to the skin 50, the depth of penetration (DOP) can also be controlled. In some embodiments, the average DOP (e.g., across the microneedles 108) can be at least 25 microns, in some embodiments, at least 50 microns, and in some embodiments, at least 100 microns. In some embodiments, the DOP can be no greater than 600 microns, in some embodiments, no greater than 300 microns, in some embodiments, no greater than 250 microns, and in some embodiments, no greater than 50 microns.

In some embodiments, at least a portion of the second portion 104 can be shaped or configured to facilitate being grasped by hand and/or to facilitate removal of the second portion 104 from the first portion 102 when the connector 106 is in its second state.

The second portion 104 can be movable (e.g., by meeting the threshold application force) with respect to the first portion 102 between:
  (i) a first (or primed, or unactuated, or treatment) position $P_1$ (see FIGS. 1 and 2A) when the connector 106 is in its first state and intact, and the applicator 100 is in its first state and configured to be applied to the skin 50, and
  (ii) a second (or actuated) position $P_2$ (see FIG. 2B, i.e., prior to removal) when the connector 106 is in its second state, and the microneedles 108 are generally inserted into the skin 50.

As shown in FIG. 2C, after the second portion 104 has been moved to the second position $P_2$, e.g., by virtue of yielding or fracturing the connector 106, the second portion 104 can optionally be removed and optionally discarded.

In some embodiments, the first portion 102 and the second portion 104 can be spaced (e.g., held) a distance apart when the second portion 104 is in its first position $P_1$ and the connector 106 (and the applicator 100) is in its first state, and no longer spaced apart (or the same distance apart) when the second portion 104 is in the second position $P_2$. For example, in some embodiments, the second portion 104, or a portion thereof, can be spaced a first distance from the first portion 102 (e.g., a vertical distance above the first portion 102, as shown in FIG. 2A) so that the first portion 102 and the second portion 104 are not in contact with one another, when the second portion 104 is in the first position $P_1$ (and the connector 106 is in its first state). In such embodiments, when the second portion 104 is in the second position $P_2$ (and the connector 106 is in its second state), second portion 104, or the portion thereof, can be spaced a second distance from the first portion 102, where the second distance is less than the first distance, such that the first portion 102 and the second portion 104 are located closer together, or the second distance is zero, such that the first portion 102 and the second portion 104 are in contact, as shown in FIG. 2B.

In some embodiments, the second portion 104 can be dimensioned to receive at least a portion of the first portion 102. By way of example only, the second portion 104 is shown as including a recess or cavity 130 (e.g., a downwardly-facing or downwardly-opening recess or cavity) that is dimensioned to receive the first portion 102 (e.g., at least when the connector 106 is in its second state). The recess 130 is at least partially defined by a lip 132 that extends around the periphery of the second portion 104 and which also defines the second major surface 114. In some embodiments, as shown, the lip 132 can extend on all sides of the second portion 104, such that the second portion 104 includes an area that is defined by an outer periphery 134 that is greater than an outer periphery 136 of the first portion 102.

As shown, in some embodiments, the connector(s) 106 can couple the outer periphery 136 of the first portion 102 and an inner wall or inner surface 138 of the second portion 104 that defines the recess 130 (e.g., a plurality of connectors 106 can be spaced apart around the outer periphery 136 of the first portion 102, as shown in FIG. 1). Particularly, the connector(s) 106 can couple an upper portion 140 of the first portion 102 and a lower portion 142 of the second portion 104 (or of the recess 130), e.g., adjacent or toward the second major surface 114. In such embodiments, the inner wall 138 of the second portion 104 can be spaced a vertical distance above the top of the first portion 102 and can be spaced a horizontal distance from the outer periphery 136 of the first portion 102.

Furthermore, in such embodiments, as shown, the connector 106 can extend substantially horizontally across the horizontal distance between the first portion 102 and the second portion 104. Such a horizontal configuration allows the connector 106 to shear in response to pressing the applicator 100 into the skin 50 in a direction substantially perpendicular to the first major surface 112, because when the connector 106 is horizontal, it is substantially parallel with the first major surface 112. However, in some embodiments, the connector 106 can extend horizontally and/or vertically between the first portion 102 and the second portion 104. In some embodiments, the connector 106 can extend between the outer periphery 136 of the first portion 102 and the inner wall 138 (or a vertical portion thereof) of the second portion 104. Said another way, in some embodiments, the connector 106 can be positioned to couple the outer periphery 136 of the first portion 102 with an inner periphery 146 of the second portion 104.

In some embodiments, the second portion 104 can have a total area or footprint that is defined by its outer periphery 134, and first portion 102 can have a total area or footprint that is defined by its outer periphery 136, and the area of the second portion 104 can be greater than that of the first portion 102.

The applicator 100 and its construction and configuration are shown by way of example only and can take on a variety of shapes and configurations as long as the applicator 100 is configured to be pressed into the skin surface 50 as a whole to puncture or perforate the skin 50 with the microneedles 108. The connector 106 is configured such that its yield or fracture strength is equal to (or less than) the threshold application force so that the connector 106 yields or fractures when the desired force (and, as a result, depth of penetration) is achieved.

Depending on the configuration of the connector 106, in some embodiments, the connector 106 can break or yield at one of its ends or in its middle. In some embodiments, the connector 106 can be released from the applicator 100 (i.e., broken off) when the connector 106 is fractured. Alternatively, in some embodiments, even when the connector 106 fractures (as opposed to yielding), at least a portion of the connector 106 can remain coupled to one or both of the first portion 102 and the second portion 104.

As shown in dashed lines in FIGS. 2A-2C, in some embodiments, the second portion 104 can be configured such that the second major surface 114 will abut the skin 50 when the second portion 104 is in the second position $P_2$, i.e., after the connector 106 has been yielded or fractured. That is, in some embodiments, the second portion 104 (or a portion thereof, e.g., the lip 132) can include an extension 115 (which can define the first major surface 114, when employed), such that the second portion 104 has a height that is greater than the height of the first portion 102 (i.e., including any portion of the microneedle device 110, such as the carrier 124) that does not puncture the skin 50). Such a configuration can allow the second portion 104 to surround, envelope and/or receive at least a portion of the first portion 102 when the applicator 100 is in its second state (and the second portion 104 is in the second position $P_2$ and the connector 106 is in its second state). As a result, if a user continues to press on the applicator 100 (e.g., second portion 104) after the connector 106 has changed to its second state, the second portion 104 (e.g., the second major surface 114) can be pressed into the skin surface 50 without causing the microneedle array 107 to continue to be pressed into the skin surface 50. The extension 115 can be useful, for example, in embodiments in which audible and/or tactile feedback is not employed with the connectors 106 to signal to a user when pressure on the applicator 100 (e.g., on the second portion 104) can be discontinued.

In some embodiments, such a configuration can allow the second portion 104 to surround, envelope and/or receive at least a portion of the first portion 102 even when the applicator 100 is in its first state (and the second portion 104 is in its first position $P_1$ and the connector 106 is in its first state) and to further surround, envelope and/or receive the first portion 102 when the applicator 100 is in its second state (and the second portion 104 is in the second position $P_2$ and the connector 106 is in its second state).

Either way, as a result, after the connector 106 is yielded or fractured, i.e., after the threshold application force has been reached or exceeded, continued pressure on the second portion 104 toward the skin 50 will only cause the second major surface 114 to continue abutting the skin 50, but will not cause continued pressure on the microneedles 108.

As shown, the applicator 100 can be configured such that at least a portion of the microneedle array 107 extends beyond the first major surface 112 and the second major surface 114, especially when the applicator 100 is in a first state, the second portion 104 is in its first position $P_1$ with respect to the first portion 102, and the connector 106 is its first state. Such a configuration allows the applicator 100 to be pressed into the skin 50 as desired to apply the microneedle array 107 into the skin 50, until the threshold application force is achieved.

While not required, in some embodiments, the second portion 104 can be substantially immovable or substantially fixed with respect to the first portion 102 when the second portion 104 is in the first position $P_1$, the applicator 100 is in its first state, and the connector 106 is in its first state; and the second portion 104 can become movable with respect to the first portion 102 after the threshold application force is met and the connector 106 is fractured or yielded, i.e., in its second state. That is, in some embodiments, the applicator 100 can be substantially rigid in its configuration until the connector 106 is fractured or yielded.

The phrase "substantially immovable" or "substantially fixed" generally refers to, in some embodiments, the first portion 102 and the second portion 104 perhaps having some element of "give," with respect to one another, but not being movable relative to one another by an appreciable amount that can be detected tactilely or visually by a user, until the connector 106 is fractured. However, in some embodiments, the first portion 102 and the second portion 104 can be movable with respect to one another even before the connector 106 is fractured, as long as the first portion 102 and the second portion 104 are still mechanically connected in such a way that allows the application force on the second portion 104 to be transmitted to the first portion 102 sufficient to press the microneedle array 107 into the skin 50, that is, until the threshold application force is met or exceeded and the connector 106 fractures. In some of such embodiments, after the connector 106 has changed to its second state, the second portion 104 can become more movable with respect to the first portion 102.

As the applicator 100 is pressed into the skin 50, a first downward force can be generated, as well as a second upward force as a result of the skin 50 resisting the first force. The connector 106 can be configured to yield or fracture when the second force is sufficient to transfer the first force to the connector 106 and when the first force (or the portion thereof transferred to the connector 106) meets or exceeds the threshold application force. That is, the connector 106 can be configured to yield or fracture when at least one of the (i) first force, (ii) the second force, and (iii) their combination, i.e., the sum of the magnitude of the first force and the magnitude of the second force, equals or exceeds the threshold application force.

During application of the applicator 100, the first major surface 112 (i.e., the skin-contact adhesive 120) can be adhered to a desired area of the skin 50. When the desired treatment and/or delivery period has lapsed, the entire applicator 100 can be removed from the skin 50 by peeling the first surface 112 (e.g., the skin-contact adhesive 120) from the skin 50. Alternatively, the skin-contact adhesive 120 can be configured to lose its adhesiveness, or tack, after a predetermined period of time, such that the applicator 100 essentially falls off of the skin 50 when it is desired for the applicator 100 to be removed.

The applicator 100 and its construction and configuration are shown by way of example only and can take on a variety of shapes and configurations as long as the applicator 100 is configured to be pressed into the skin surface 50 as a whole to puncture or perforate the skin 50 with the microneedles 108. The connector 106 is configured such that its yield or fracture strength is equal to (or less than) the threshold application force so that the connector 106 yields or fractures when the desired force (and, as a result, depth of penetration) is achieved.

In use, methods of applying the applicator 100 to the skin surface 50 can include pressing the applicator 100 (e.g., as a whole, e.g., by pressing on the second portion 104) in a direction substantially perpendicular to the first major surface 112 (and, optionally, with respect to the second major surface 114) to press the microneedle array 107 into the skin surface 50 until the threshold application force is met or exceeded and the connector 106 is yielded or fractured, i.e., changed to its second state. Methods of applying the applicator 100 can further include removing the second portion 104 from the applicator 100 (or from the first portion 102) when the connector 106 is in its second state. Methods can further include leaving the first portion 102 on the skin surface 50 with the microneedle array 107 for a treatment period after removing the second portion 104.

Pressing the applicator 100 into the skin surface 50 can generate a first force generally directed toward the skin surface 50 and a second force generated by the resistance of the skin surface 50 that generally opposes the first force. The connector 106 can change to its second state when at least one of the first force, the second force, and the sum of the magnitude of the first force and the magnitude of the second force equals or exceeds the threshold application force.

Pressing the applicator 100 into the skin surface 50 can include pressing the second portion 104 with respect to the first portion 102 to move the second portion 104 from its first position $P_1$ relative to the first portion 102 in which the connector 106 is intact (and the second portion 104 is optionally substantially fixed relative to the first portion 102), to its second position $P_2$ relative to the first portion 102 in which the connector 106 is in its second state (and the second portion 104, optionally, is movable with respect to (e.g., removable from) the first portion 102).

As mentioned above, in some embodiments, active ingredients or agents (e.g., drugs) can be delivered via the microneedles 108 (e.g., via solid microneedles, as described below). Examples of pharmaceutically active agents (also referred to as "drugs") that can be incorporated into the applicators of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl] methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; anti-obesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the microneedles 108 (e.g., via solid microneedles). Examples of peptide therapeutic agents that can be incorporated into the applicators of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e.g. IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049120 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

In some embodiments, as shown in FIG. 1, the skin-contact adhesive 120 can cover the entire non-treatment region(s) 113 of the first major surface 112. Alternatively, in some embodiments, the skin-contact adhesive 120 can partially cover the non-treatment region(s) 113 of the first major surface 112, e.g., including intermittent application of the skin-contact adhesive 120 to create gaps (e.g., randomly, or in a pattern), and/or a complete ring of skin-contact adhesive 120 that has a width that is less than the width of the illustrated non-treatment region 113 of the first surface 112.

The skin-contact adhesive 120 is generally a pressure-sensitive adhesive, and particularly is a pressure-sensitive adhesive that is capable of securely but releasably adhering or bonding to skin (e.g., mammalian skin). The skin-contact adhesive 120 is also generally safe and non-toxic. Skin-contact adhesive layers will generally be selected according to the desired end use of the applicator 100. In some embodiments, the applicator 100 can include more than one skin-contact adhesive 120. Where the applicator 100 comprises more than one skin-contact adhesive layer 120, each skin-contact adhesive layer 120 may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesives 120. In general, the skin-contact adhesive 120 should cause little or no irritation or sensitization of the skin during the intended wear period.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049150 (Dalton et al.), the disclosure of which is hereby incorporated by reference.

In some embodiments, the acrylate copolymer can comprise the reaction product of primary and polar monomers and additional optional monomers which, when present, are included in the polymerization reaction in quantities that will not render the adhesive composition non-tacky. The optional additional monomers may be added, for example, to improve performance, reduce cost, or for other purposes. Examples of such optional monomers include vinyl esters, such as vinyl acetate, vinyl chloride, vinylidene chloride, styrene, and macromonomers copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference.

Silicone or polysiloxane pressure-sensitive adhesives include pressure-sensitive adhesives which are based on two major components: a polymer, or gum, and a tackifying resin. The polysiloxane adhesive can be prepared by cross-linking the gum, typically a high molecular weight polydiorganosiloxane, with the resin, to produce a three-dimensional silicate structure, via a condensation reaction in an appropriate organic solvent. The ratio of resin to polymer can be adjusted in order to modify the physical properties of polysiloxane adhesives. Use of capped (or amine-compatible) polysiloxanes can, in some embodiments, be preferred so as to increase drug stability and reduce degradation. Further details and examples of silicone pressure-sensitive adhesives which can be useful are described in the U.S. Pat. No. 4,591,622 (Blizzard et al.); U.S. Pat. No. 4,584,355 (Blizzard et al.); U.S. Pat. No. 4,585,836 (Homan et al.); and U.S. Pat. No. 4,655,767 (Woodard et al.). Suitable silicone pressure-sensitive adhesives are commercially available and include the silicone adhesives sold under the trademarks BIO-PSA® by Dow Corning Corporation, Medical Products, Midland, Mich.

Further description of suitable adhesives may be found in U.S. Pat. No. 5,656,286 (Miranda et al.), U.S. Pat. No. 5,223,261 (Nelson et al.), and U.S. Pat. No. 5,380,760 (Wendel et al.), the disclosures of which are incorporated herein by reference. In some embodiments, the thickness of the skin-contact adhesive 120 can be at least about 10 µm, in some embodiments, at least about 20 µm, and in some embodiments, at least about 40 µm. In some embodiments, the thickness of the skin-contact adhesive 120 can be less than about 2 mm (0.07874 inch), in some embodiments, less than about 1 mm (0.03937 inch), and in some embodiments, less than about 120 microns (5906 microinches).

In some embodiments, a medical grade adhesive can be preferred for the skin-contact adhesive 120. Such a medical grade skin-contact adhesive 120 is can have physical properties and characteristics to be capable of maintaining intimate contact with the skin 50 throughout the desired treatment and/or delivery period. Securing the first portion 102 to the skin 50 can aid in keeping the microneedles 108 inserted into the skin 50.

In embodiments employing the skin-contact adhesive 120, a release liner (not shown) can be coupled to the skin-contact adhesive 120 prior to use and removed when it is desired to apply the applicator 100 to the skin 50.

Release liners are available from a variety of manufacturers in a wide variety of proprietary formulations. Those skilled in the art will normally test those liners in simulated use conditions against an adhesive of choice to arrive at a product with the desired release characteristics. Liners which can be suitable for use in applicators of the present disclosure can be made of kraft papers, polyethylene, polypropylene, polyester or composites of any of these materials. The liner material can be coated with release agents or low adhesion coatings, such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials. Examples of commercially available silicone coated release papers are POLYSLIK® silicone release papers available from Loparex (Willowbrook, Ill.).

In some embodiments, the length of time that the applicator 100 remains on the skin 50 may be an extended time, for example, from about 12 hours to about 14 days. In some embodiments, the duration of time that the applicator 100 remains on the skin 50 can be about 1 day (i.e., daily dosing), about 3 to 4 days (i.e., bi-weekly dosing), or about 7 days (i.e., weekly dosing).

In some embodiments, the duration of time that the applicator 100 remains on the skin 50 may be relatively short, for example from about 1 minute to about 1 hour, in some embodiments, from about 5 minutes to about 40 minutes, and in some embodiments, from about 5 minutes to about 20 minutes.

In some embodiments, the microneedles 108 can be solid. In such embodiments, if an active agent is to be delivered to the skin, the active agent can be applied to the microneedles 108 by applying an active agent prior to applicator assembly, e.g., by coating, etc. In some embodiments, the microneedles 108 can be hollow. In such embodiments, the applicator 100 can further include one or more supply reservoirs or chambers comprising the active agent that can be fluidly coupled to hollow channels in the microneedles 108, such that the active agent can be delivered (e.g., continuously, at a desired rate, over a desired period of time) to the skin 50 via the hollow channels in the microneedles 108. Additionally or alternatively, in some embodiments, when hollow microneedles 108 are employed, the applicator 100 can be coupled to a supply device (e.g., a syringe, a unit dose delivery device, a suitable metering pump, an infusion device for delivering an agent at a controlled rate, other suitable supply devices, or combinations thereof) that can be fluidly coupled to hollow channels in the microneedles 108 to drive delivery of the active agent through hollow channels in the microneedles 108 into the skin 50.

Microneedle arrays useful for practicing the present disclosure can have a variety of configurations and features, such as those described in the following patents and patent applications, the disclosures of which are incorporated herein by reference. One embodiment for the microneedle arrays includes the structures disclosed in U.S. Patent Application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin. Still another embodiment for the microneedle arrays includes the structures disclosed in U.S. Pat. No. 6,312,612 (Sherman et al.), which describes tapered structures having a hollow central channel. Yet still another embodiment for the microneedle arrays includes the structures disclosed in U.S. Pat. No. 6,379,324 (Garstein et al.), which describes hollow microneedles having at least one longitudinal blade at the top surface of the tip of the microneedle. A further embodiment for the microneedle arrays includes the structures disclosed in U.S. Patent Application Publication Nos. US2012/0123387 (Gonzalez et al.) and US2011/0213335 (Burton et al.), which both describe hollow microneedles. A still further embodiment for the microneedle arrays includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure.

In some embodiments, the microneedle material can be (or include) silicon, glass, or a metal such as stainless steel, titanium, or nickel titanium alloy. In some embodiments, the microneedle material can be (or include) a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In some embodiments, the microneedles can be made from (or include) a combination of two or more of any of the above mentioned materials. For example, the tip of a microneedle may be a dissolvable material, while the remainder of the microneedle is a medical grade polymeric material.

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). In a preferred embodiment, the plurality of microneedles in a microneedle array each have a square pyramidal shape.

In some embodiments, the plurality of microneedles in a microneedle array are solid microneedles (that is, the microneedles are solid throughout). In some embodiments, the plurality of solid microneedles in a solid microneedle array can have a square pyramidal shape, triangular pyramidal shape, stepped pyramidal shape, conical shape, or microblade shape. In a preferred embodiment, the plurality of solid microneedles in a solid microneedle array each have a square pyramidal shape.

In some embodiments, the plurality of microneedles in a microneedle array are hollow microneedles (that is, the microneedles contain a hollow bore through the microneedle). The hollow bore can be from the base of the microneedle to the tip of the microneedle or the bore can be from the base of the microneedle to a position offset from the tip of the microneedle. In some embodiments, one or more of the plurality of hollow microneedles in a hollow microneedle array can have a conical shape, cylindrical shape, square pyramidal shape, triangular pyramidal shape, or the shape of a hypodermic needle.

In some embodiments, one or more of the plurality of hollow microneedles in a hollow microneedle array can have a conical shape. In some embodiments, one or more of the plurality of hollow microneedles in a hollow microneedle array can have a cylindrical shape. In some embodiments, one or more of the plurality of hollow microneedles in a hollow microneedle array can have a square pyramidal shape. In some embodiments, one or more of the plurality of hollow microneedles in a hollow microneedle array can have a triangular pyramidal shape. In some embodiments, one or more of the plurality of hollow microneedles in a hollow microneedle array can have the shape of a hypodermic needle. In a preferred embodiment, the plurality of hollow microneedles in a hollow microneedle array each have the shape of a conventional hypodermic needle.

Figure 6:
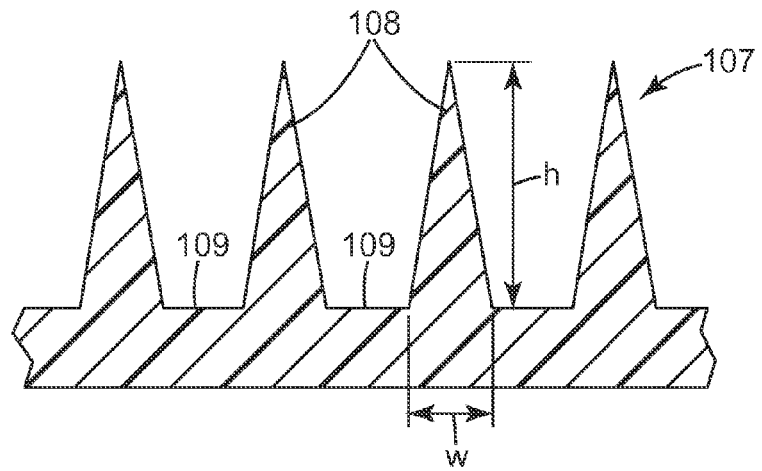
FIG. 6 is a close-up side cross-sectional view of the microneedle array of FIGS. 1-2C (shown with the microneedles pointing upwardly).

FIG. 6 shows a portion of the microneedle array 107 that includes four microneedles 108 (of which two are referenced in FIG. 6) positioned on a microneedle substrate 109. Each microneedle 108 has a height h, which is the length from the tip of the microneedle 108 to the microneedle base at substrate 109. Either the height of a single microneedle or the average height of all microneedles on the microneedle array can be referred to as the height of the microneedle, h. In some embodiments, each of the plurality of microneedles (or the average of all of the plurality of microneedles) has a height of about 100 to about 3000 micrometers, in some embodiments, about 100 to about 1200 micrometers, in some embodiments, about 100 to about 1200 micrometers, and, in some embodiments, about 100 to about 1000 micrometers.

In some embodiments, each of the plurality of microneedles (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1200 micrometers, about 500 to about 1000 micrometers, or about 500 to about 750 micrometers.

In some embodiments, each of the plurality of microneedles (or the average of all of the plurality of microneedles) has a height of about 800 to about 1400 micrometers.

In some embodiments, each of the plurality of microneedles (or the average of all of the plurality of microneedles) has a height of about 500.

In some embodiments, each of the plurality of microneedles (or the average of all of the plurality of microneedles) has a height of less than about 3000 micrometers. In other embodiments, each of the plurality of microneedles (or the average of all of the plurality of microneedles) has a height of less than about 1200 micrometers. In still other embodiments, each of the plurality of microneedles (or the average of all of the plurality of microneedles) has a height of less than about 1200 micrometers. In yet still other embodiments, each of the plurality of microneedles (or the average of all of the plurality of microneedles) has a height of less than about 1000 micrometers. In further embodiments, each of the plurality of microneedles (or the average of all of the plurality of microneedles) has a height of less than about 750 micrometers. In still further embodiments, each of the plurality of microneedles (or the average of all of the plurality of microneedles) has a height of less than about 600 micrometers.

In some embodiments, each of the plurality of microneedles (or the average of all of the plurality of microneedles) has a height of at least about 100 micrometers. In other embodiments, each of the plurality of microneedles (or the average of all of the plurality of microneedles) has a height of at least about 200 micrometers. In still other embodiments, each of the plurality of microneedles (or the average of all of the plurality of microneedles) has a height of at least about 250 micrometers. In further embodiments, each of the plurality of microneedles (or the average of all of the plurality of microneedles) has a height of at least about 500 micrometers. In still further embodiments, each of the plurality of microneedles (or the average of all of the plurality of microneedles) has a height of at least about 800 micrometers.

In some embodiments employing solid microneedles, each of the plurality of solid microneedles (or the average of all of the plurality of solid microneedles) has a height of about 100 to about 1200 micrometers, about 100 to about 1200 micrometers, about 200 to about 1000 micrometers, about 200 to about 750 micrometers, about 200 to about 600 micrometers, or about 500 micrometers.

In some embodiments employing hollow microneedles, each of the plurality of hollow microneedles (or the average of all of the plurality of hollow microneedles) has a height of about 100 to about 3000 micrometers, about 800 to about 1400 micrometers, or about 500 micrometers.

In some embodiments, each of the plurality of hollow microneedles (or the average of all of the plurality of hollow microneedles) has a height of about 900 to about 1000 micrometers. In other embodiments, each of the plurality of hollow microneedles (or the average of all of the plurality of hollow microneedles) has a height of about 900 to about 950 micrometers. In still other embodiments, each of the plurality of hollow microneedles (or the average of all of the plurality of hollow microneedles) has a height of about 900 micrometers.

A single microneedle or the plurality of microneedles in a microneedle array can also be characterized by their aspect ratio. The aspect ratio of a microneedle is the ratio of the height of the microneedle, h to the width (at the base of the microneedle), w (as shown in FIG. 6). The aspect ratio can be presented as h:w. In some embodiments, each of the plurality of microneedles (or the average of all the plurality of microneedles) has (have) an aspect ratio in the range of 2:1 to 5:1. In some of these embodiments, each of the plurality of microneedles (or the average of all of the plurality of microneedles) has (have) an aspect ratio of at least 3:1.

In some embodiments, the array of microneedles contains about 100 to about 1200 microneedles per cm$^2$ of the array of microneedles.

In some embodiments employing solid microneedles, the array of solid microneedles contains about 100 to about 1200 solid microneedles per cm$^2$ of the array of solid microneedles.

In some embodiments, the array of solid microneedles contains about 200 to about 500 solid microneedles per cm$^2$ of the array of solid microneedles.

In some embodiments, the array of solid microneedles contains about 300 to about 400 solid microneedles per cm$^2$ of the array of solid microneedles.

In some embodiments employing hollow microneedles, the array of hollow microneedles contains about 3 to about 30 hollow microneedles per array of hollow microneedles.

In some embodiments, the array of hollow microneedles contains about 10 to about 30 hollow microneedles per array of hollow microneedles.

In some embodiments, the array of hollow microneedles contains about 3 to about 20 hollow microneedles per array of hollow microneedles.

In some embodiments, the array of hollow microneedles contains about 13 to about 20 hollow microneedles per array of hollow microneedles.

In some embodiments, the array of hollow microneedles contains about 8 to about 18 hollow microneedles per array of hollow microneedles.

In some embodiments, the array of hollow microneedles contains about 18 hollow microneedles per array of hollow microneedles.

In some embodiments, the array of hollow microneedles contains about 12 hollow microneedles per array of hollow microneedles.

In some embodiments, each of the plurality of microneedles (or the average of all of the plurality of microneedles) in a microneedle array can penetrate into the skin to a depth of about 50 to about 1200 micrometers, about 50 to about 400 micrometers, or about 50 to about 250 micrometers.

In some embodiments, each of the plurality of microneedles (or the average of all of the plurality of microneedles) in a microneedle array can penetrate into the skin to a depth of about 100 to about 400 micrometers, or about 100 to about 300 micrometers.

In some embodiments, each of the plurality of microneedles (or the average of all of the plurality of microneedles) in a microneedle array can penetrate into the skin to a depth of about 120 to about 1200 micrometers, or about 800 to about 1200 micrometers.

In some embodiments, each of the plurality of microneedles (or the average of all of the plurality of microneedles) in a microneedle array can penetrate into the skin to a depth of about 400 to about 800 micrometers.

For all of the above embodiments, it will be appreciated that the depth of penetration (DOP) of each of the plurality of microneedles (or the average of all of the plurality of microneedles) in a microneedle array may not be the full length of the microneedles themselves.

For hollow microneedles, a hollow channel or bore extends through the substrate 109, 109A and microneedles 108, 108A. In some embodiments, the bore exits at a channel opening at or near the tip of the hollow microneedle. The channel preferably exits at an opening near the tip of the hollow microneedle. Most preferably, the channel or bore continues along a central axis of the microneedle, but exits similar to a hypodermic needle on a sloping side-wall of the microneedle to help prevent blockage of the channel by tissue upon insertion. In some embodiments, the diameter of the channel bore is about 10 to about 200 micrometers. In other embodiments, the diameter of the channel bore is about 10 to about 120 micrometers. In still other embodiments, the diameter of the channel bore is about 30 to about 60 micrometers.

In some embodiments of hollow microneedles, the average cross-sectional area of the channel bore is about 75 to about 32,000 micrometers. In other embodiments of hollow microneedles, the average cross-sectional area of the channel bore is about 75 to about 18,000 micrometers. In still other embodiments of hollow microneedles, the average cross-sectional area of the channel bore is about 700 to about 3,000 micrometers.

In some embodiments of hollow microneedle arrays, the average spacing between adjacent microneedles (as measured from microneedle tip to microneedle tip) is between about 0.7 mm and about 20 mm. In other embodiments of hollow microneedle arrays, the average spacing between adjacent microneedles is between about 0.7 mm and about 10 mm. In still other embodiments of hollow microneedle arrays, the average spacing between adjacent microneedles is between about 2 mm and about 20 mm. In still other embodiments of hollow microneedle arrays, the average spacing between adjacent microneedles is between about 2 mm and about 10 mm. In a preferred embodiment of hollow microneedle arrays, the average spacing between adjacent microneedles is between about 2 mm.

In some embodiments of hollow microneedle arrays, the average spacing between adjacent microneedles (as measured from microneedle tip to microneedle tip) is greater than about 0.7 mm. In other embodiments of hollow microneedle arrays, the average spacing between adjacent microneedles is greater than about 2 mm.

In some embodiments of hollow microneedle arrays, the average spacing between adjacent microneedles is less than about 20 mm. In other embodiments of hollow microneedle arrays, the average spacing between adjacent microneedles is less than about 10 mm.

In some embodiments of solid microneedle arrays, the average spacing between adjacent microneedles (as measured from microneedle tip to microneedle tip) is between about 200 micrometers and about 2000 micrometers. In other embodiments of solid microneedle arrays, the average spacing between adjacent microneedles is between about 200 micrometers and about 600 micrometers. In still other embodiments of solid microneedle arrays, the average spacing between adjacent microneedles is between about 200 micrometers and about 300 micrometers. In yet still other embodiments of solid microneedle arrays, the average spacing between adjacent microneedles is between about 500 micrometers and about 600 micrometers.

In some embodiments of solid microneedle arrays, the average spacing between adjacent microneedles (as measured from microneedle tip to microneedle tip) is greater than about 200 micrometers. In other embodiments of solid microneedle arrays, the average spacing between adjacent microneedles is greater than about 500 micrometers.

In some embodiments of solid microneedle arrays, the average spacing between adjacent microneedles is less than about 2000 micrometers. In other embodiments of solid microneedle arrays, the average spacing between adjacent microneedles is less than about 1000 micrometers. In still other embodiments of solid microneedle arrays, the average spacing between adjacent microneedles is less than about 600 micrometers. In yet still other embodiments of solid microneedle arrays, the average spacing between adjacent microneedles is less than about 300 micrometers.

The microneedle arrays can be manufactured in any suitable way such as by injection molding, compression molding, metal injection molding, stamping, photolithography, or extrusion. In one embodiment, hollow microneedle arrays can be made by thermocycled injection molding of a polymer such as medical grade polycarbonate or LCP, followed by laser drilling to form the channels of the microneedles.

Additional exemplary embodiments of applicators of the present disclosure will now be described with respect to FIGS. 3-5B. FIGS. 3-5B illustrate various applicators of the present disclosure, wherein like numerals represent like elements. The applicators of FIGS. 3-5B share many of the same elements, features, and functions as those described above with respect to FIGS. 1-2C. Reference is made to the description above accompanying FIGS. 1-2C for a more complete description of the features and elements (and alternatives to such features and elements) of the embodiments illustrated in FIGS. 3-5B. Any of the features described above with respect to FIGS. 1-2C can be applied to the embodiments of FIGS. 3-5B, and vice versa.

Figure 3:
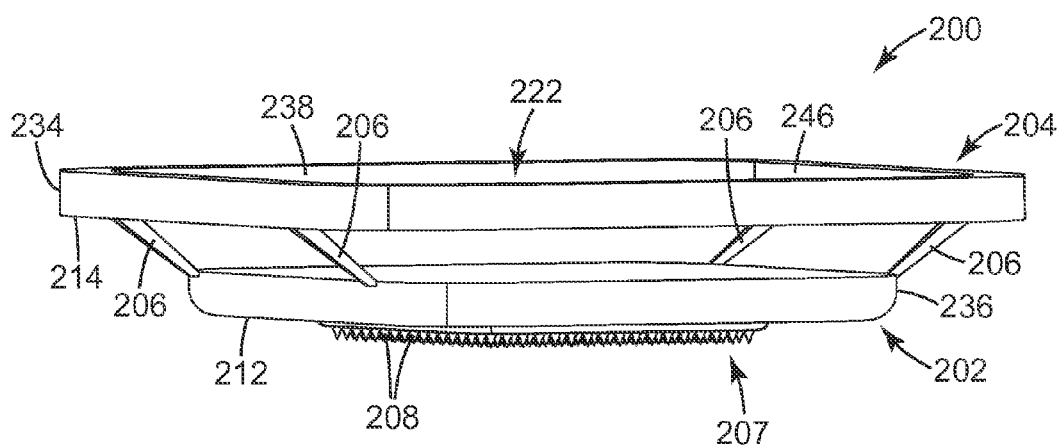
FIG. 3 is a perspective view of an applicator according to another embodiment of the present disclosure, the applicator shown unactuated and comprising a first portion comprising a microneedle array; a second portion; and a connector, shown in a first state, coupling the first portion and the second portion; the second portion shown in a first position relative to the first portion.

FIG. 3 illustrates an applicator 200 according to another embodiment of the present disclosure. FIG. 3 shows the applicator 200 in its first (or primed, or unactuated, or treatment) state. The applicator 200 includes a first portion 202 and a second portion 204 coupled to the first portion 202 via one or more connectors 206 (four connectors 206 are shown by way of example only). As shown, the first portion 202 includes a microneedle array 207 comprising microneedles 208 that protrude from a first major surface 212 of the first portion 202. The second portion 204 can also include a second major surface 214, and the first major surface 212 and the second major surface 214 can each be configured to be substantially parallel with a skin surface to which the applicator 100 will be applied, and are generally configured to be positioned toward, or facing, the skin surface. As shown, when the connectors 206 are intact and in their first state, at least a portion of the microneedle array 207 extends beyond both the first major surface 212 and the second major surface 214.

The applicator 200 is configured to be pressed as a whole (e.g., by pressing on the second portion 204) in a direction substantially perpendicular to the first major surface 212 (and, optionally, the second major surface 214) to press the microneedle array 207 into a skin surface (e.g., to within a specified range of depths under a specified range of forces) until the threshold application force is reached and the connector(s) 206 yield or fractures.

The overall configuration and function of the applicator 200 of FIG. 3 is substantially similar to the applicator 100 of FIGS. 1-2C described above, except that the first portion 202 and the second portion 204 are spaced a greater distance apart from one another, the connectors 206 are longer as a result, and the second portion 204 includes an opening 222 formed therethrough that is dimensioned to receive at least a portion of the first portion 202.

As shown in FIG. 3, the first portion 202 and the second portion 204 can be spaced a greater distance apart, both horizontally and vertically, and the connectors 206 can extend at least partially horizontally and at least partially vertically between the first portion 202 and the second portion 204.

Because of the opening 222 in the second portion 204, when the second portion 204 is moved from a first position (shown in FIG. 3) in which the connectors 206 are intact (i.e., in their first state) and the applicator 200 is in its first state to a second position in which the connectors 206 are in their second state and the applicator 200 is in its second state, the first portion 202 can pass at least partially through the opening 222 in the second portion 204. In addition, after the connectors 206 are changed to their second state, the first portion 202 and the second portion 204 no longer have any overlapping portions, such that any continued pressure on the second portion 204 into skin would not be transferred to the first portion 202, and the second portion 204 can cleanly and easily be removed, and optionally, discarded. As a result, after the connector 206 is yielded or fractured, i.e., after the threshold application force has been reached or exceeded, continued pressure on the second portion 204 toward the skin will only cause the second major surface 214 to continue abutting the skin, but will not cause continued pressure on the microneedles 208.

Furthermore, as shown in FIG. 3, the opening 222 can be defined at least partially by an inner wall or surface 238 of the second portion 204. In some embodiments, as shown, the one or more connectors 106 can extend between an outer periphery 236 of the first portion 202 and the inner wall 238 of the second portion 204. Said another way, in some embodiments, the connector 206 can be positioned to couple the outer periphery 236 of the first portion 202 with an inner periphery 246 of the second portion 204.

In some embodiments, the second portion 204 can have a total area or footprint that is defined by an outer periphery 234, and first portion 202 can have a total area or footprint that is defined by its outer periphery 236, and the area of the second portion 204 can be greater than that of the first portion 202. As a result of the larger area or footprint of the second portion 204 and the opening 222 in the second portion 204, the second portion 204 can surround, envelope and/or receive at least a portion of the first portion 202 at least when the applicator 200 is in its second state (and the second portion 204 is in a second position and the connector 206 is in its second state).

The applicator 200 and its construction and configuration are shown by way of example only and can take on a variety of shapes and configurations as long as the applicator 200 is configured to be pressed into a skin surface as a whole to puncture or perforate the skin with the microneedles 208. The connector 206 is configured such that its yield or fracture strength is equal to (or less than) the threshold application force so that the connector 206 yields or fractures when the desired force (and, as a result, depth of penetration) is achieved.

In use, methods of applying the applicator 200 to a skin surface can include pressing the applicator 200 (e.g., as a whole, e.g., by pressing on the second portion 204) in a direction substantially perpendicular to the first major surface 212 (and, optionally, with respect to the second major surface 214) to press the microneedle array 207 into the skin surface until the threshold application force is met or exceeded and the connector(s) 206 are yielded or fractured, i.e., changed to their second state. Methods of applying the applicator 200 can further include removing the second portion 204 from the applicator 200 (or from the first portion 202) when the connector 206 is in its second state. Methods can further include leaving the first portion 202 on the skin surface with the microneedle array 207 for a treatment period after removing the second portion 204.

Pressing the applicator 200 into the skin surface can generate a first force generally directed toward the skin surface and a second force generated by the resistance of the skin surface that generally opposes the first force. The connector(s) 206 can change to their second state when at least one of the first force, the second force, and the sum of the magnitude of the first force and the magnitude of the second force equals or exceeds the threshold application force.

Pressing the applicator 200 into the skin surface can include pressing the second portion 204 with respect to the first portion 202 to move the second portion 204 from its first position relative to the first portion 202 in which the connector(s) 206 are intact (and the second portion 204 is optionally substantially fixed relative to the first portion 202), to its second position relative to the first portion 202 in which the connector(s) 206 are in their second state (and the second portion 204, optionally, is movable with respect to (e.g., removable from) the first portion 202).

Figure 4:
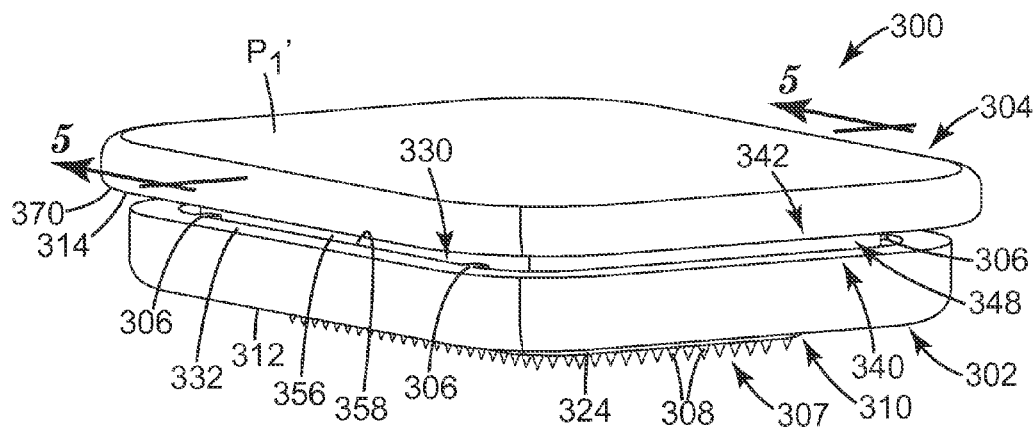
FIG. 4 is a perspective view of an applicator according to another embodiment of the present disclosure, the applicator shown unactuated and comprising a first portion comprising a microneedle array; a second portion; and a connector, shown in a first state, coupling the first portion and the second portion; the second portion shown in a first position relative to the first portion.
Figure 5A:
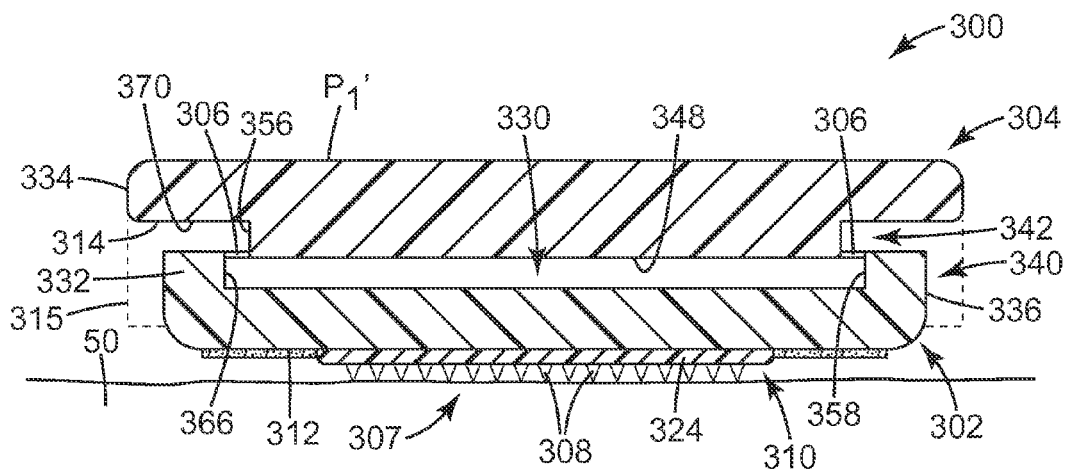
FIG. 5A is a side cross-sectional view of the applicator of FIG. 4, taken along line 5-5 of FIG. 4, the applicator shown as it is being applied to a skin surface, with the second portion in the first position, the connector in its first state, and the microneedles of the microneedle array penetrating the skin.
Figure 5B:
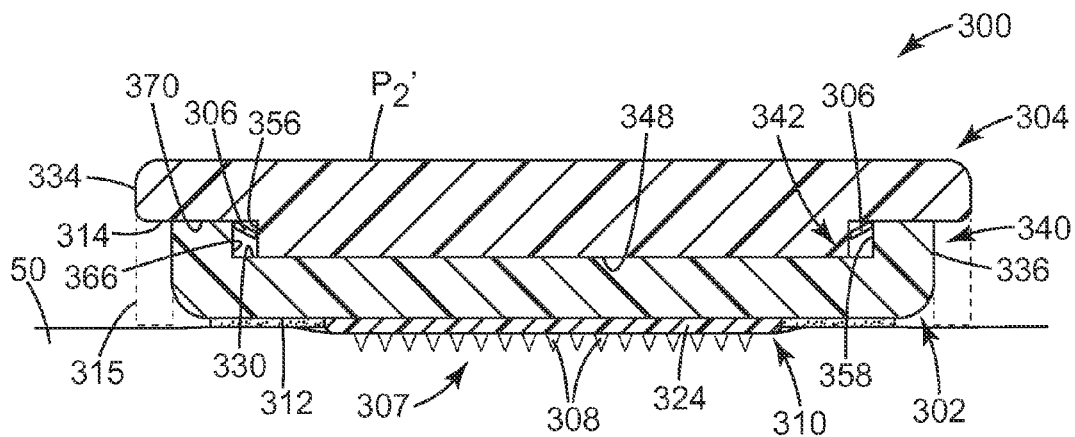
FIG. 5B is a side cross-sectional view of the applicator of FIGS. 4 and 5A, taken along line 5-5 of FIG. 4, with the second portion in a second position relative to the first portion and the connector in a second state.

FIGS. 4-5B illustrate an applicator 300 according to another embodiment of the present disclosure. The applicator 300 includes a first portion 302 and a second portion 304 coupled to the first portion 302 via one or more connectors 306. The applicator 300 includes four connectors 306 by way of example only. As shown, the first portion 302 includes a microneedle array 307 comprising microneedles 308 that protrude from a first major surface 312 of the first portion 302. The second portion 304 can also include a second major surface 314, and the first major surface 312 and the second major surface 314 can each be configured to be substantially parallel with a skin surface 50 (see FIGS. 5A and 5B) to which the applicator 300 will be applied, and are generally configured to be positioned toward, or facing, the skin surface 50. As shown, when the connectors 306 are intact and in their first state, at least a portion of the microneedle array 307 extends beyond both the first major surface 312 and the second major surface 314.

FIGS. 4 and 5A show the applicator 300 in a first (or primed, or unactuated, or treatment) state, the second portion 304 in a first position $P_1'$ with respect to the first portion 302, and the connectors 306 in a first, intact, state. FIG. 5A also shows the applicator 300 as it is about to be applied to skin, or a skin surface, 50. FIG. 5B shows the applicator 300 after the microneedles 308 have punctured the skin 50 and the threshold application force has been met, i.e., with the applicator 300 in an actuated state, the second portion 304 in a second position $P_2'$ with respect to the first portion 302, and the connectors 306 in a second (i.e., yielded or fractured) state. After the situation shown in FIG. 5B, the second portion 304 can be removed (e.g., as shown in FIG. 2C), and the first portion 302 can be left on the skin 50 for a desired treatment and/or delivery period.

The applicator 300 is configured to be pressed as a whole (e.g., by pressing on the second portion 304) in a direction substantially perpendicular to the first major surface 312 (and, optionally, the second major surface 314) to press the microneedle array 307 into the skin surface 50 (e.g., to within a specified range of depths under a specified range of forces) until the threshold application force is reached and the connector 306 yields or fractures.

The overall configuration and function of the applicator 300 of FIGS. 4-5B is substantially similar to the applicator 100 of FIGS. 1-2C described above, except that the first portion 202 includes a recess or cavity 330 (e.g., an upwardly-facing or upwardly-opening recess or cavity) dimensioned to receive at least a portion of the second portion 304, and the second portion 304 includes a portion (e.g., a downwardly-extending projection) 348 dimensioned to be received in the recess 330 (e.g., at least when the connector 306 is in its second state). The recess 330 is at least partially defined by a lip 332 that extends around the periphery of the first portion 302.

As shown, in some embodiments, the connector(s) 306 can couple an outer periphery 356 of the second portion 304 (e.g., an outer periphery of the projection 348) and an inner wall or inner surface 358 of the first portion 302 that defines the recess 330 (e.g., a plurality of connectors 306 can be spaced apart around the outer periphery 356 of the second portion 304, as shown in FIG. 4). Particularly, the connector(s) 306 can couple an upper portion 340 of the first portion 302 (or of the recess 330) and a lower portion 342 of the second portion 304 (or the portion 348). In such embodiments, the inner wall 358 of the first portion 302 can be spaced a vertical distance below the bottom of the second portion 304 and can be spaced a horizontal distance from the outer periphery 356 of the second portion 304.

Furthermore, in such embodiments, as shown, the connector 306 can extend substantially horizontally across the horizontal distance between the first portion 302 (e.g., the inner wall 358 that defines the recess 330) and the second portion 304 (e.g., the portion 348). Such a horizontal configuration allows the connector 306 to shear in response to pressing the applicator 300 into the skin 50 in a direction substantially perpendicular to the first major surface 312, because when the connector 306 is horizontal, it is substantially parallel with the first major surface 312. However, in some embodiments, the connector 306 can extend horizontally and/or vertically between the first portion 302 and the second portion 304. In some embodiments, the connector 306 can extend between the outer periphery 356 of the second portion 304 and the inner wall 358 (or a vertical portion thereof) of the first portion 302. Said another way, in some embodiments, the connector 306 can be positioned to couple the outer periphery 356 of the second portion 304

(e.g., of the portion 348) with an inner periphery 366 of the first portion 302 (e.g., with the recess 330).

As shown, even in embodiments in which the second portion 304 includes the portion 348 that is pressed down into and at least partially received in the recess 330 of the first portion 302 when the applicator 300 is actuated (i.e., when the connector(s) 306 are changed to their second state), the second portion 304 can include a flange or extension 370 that defines at least a portion of the second major surface 314 and which facilitates the second portion 304 being grasped by a user (e.g., during pressing into the skin surface 50 and also in removing the second portion 304 from the first portion 302 after the connector(s) have changed to their second state. As a result, the second portion 304 can still have a total area or footprint that is defined by an outer periphery 334, and first portion 302 can have a total area or footprint that is defined by an outer periphery 336, and the area of the second portion 304 can be greater than that of the first portion 302.

As shown in dashed lines in FIGS. 5A-5B, in some embodiments, the second portion 304 can be configured such that the second major surface 314 will abut the skin 50 when the second portion 304 is in the second position $P_2'$, i.e., after the connector 306 has been yielded or fractured. That is, in some embodiments, the second portion 304 (or a portion thereof, e.g., the flange 370) can include an extension 315 (which can define the first major surface 314, when employed), such that the second portion 304 has a height that is greater than the height of the first portion 302 (i.e., including any portion of the microneedle device 310 that does not insert into the skin 50, such as the carrier 324). Such a configuration can allow the second portion 304 to surround, envelope and/or receive at least a portion of the first portion 302 when the applicator 300 is in its second state (and the second portion 304 is in the second position $P_2'$ and the connector 306 is in its second state). As a result, if a user continues to press on the applicator 300 (e.g., second portion 304) after the connector 306 has changed to its second state, the second portion 304 (e.g., the second major surface 314) can be pressed into the skin surface 50 without causing the microneedle array 307 to continue to be pressed into the skin surface 50.

In some embodiments, such a configuration can allow the second portion 304 to surround, envelope and/or receive at least a portion of the first portion 302 even when the applicator 300 is in its first state (and the second portion 304 is in its first position $P_1'$ and the connector 306 is in its first state) and to further surround, envelope and/or receive the first portion 302 when the applicator 300 is in its second state (and the second portion 304 is in the second position $P_2'$ and the connector 306 is in its second state).

Either way, as a result, after the connector 306 is yielded or fractured, i.e., after the threshold application force has been reached or exceeded, continued pressure on the second portion 304 toward the skin 50 will only cause the second major surface 314 to continue abutting the skin 50, but will not cause continued pressure on the microneedles 308.

As shown, the applicator 300 can be configured such that at least a portion of the microneedle array 307 extends beyond the first major surface 312 and the second major surface 314, especially when the applicator 300 is in a first state, the second portion 304 is in its first position $P_1'$ with respect to the first portion 302, and the connector 306 is its first state. Such a configuration allows the applicator 300 to be pressed into the skin 50 as desired to apply the microneedle array 307 into the skin 50, until the threshold application force is achieved.

The applicator 300 and its construction and configuration are shown by way of example only and can take on a variety of shapes and configurations as long as the applicator 300 is configured to be pressed into a skin surface as a whole to puncture or perforate the skin with the microneedles 308. The connector 306 is configured such that its yield or fracture strength is equal to (or less than) the threshold application force so that the connector 306 yields or fractures when the desired force (and, as a result, depth of penetration) is achieved.

In use, methods of applying the applicator 300 to a skin surface 50 can include pressing the applicator 300 (e.g., as a whole, e.g., by pressing on the second portion 304) in a direction substantially perpendicular to the first major surface 312 (and, optionally, with respect to the second major surface 314) to press the microneedle array 307 into the skin surface 50 until the threshold application force is met or exceeded and the connector(s) 306 are yielded or fractured, i.e., changed to their second state. Methods of applying the applicator 300 can further include removing the second portion 304 from the applicator 300 (or from the first portion 302) when the connector 306 is in its second state. Methods can further include leaving the first portion 302 on the skin surface with the microneedle array 307 for a treatment period after removing the second portion 304.

Pressing the applicator 300 into the skin surface can generate a first force generally directed toward the skin surface and a second force generated by the resistance of the skin surface that generally opposes the first force. The connector(s) 306 can change to their second state when at least one of the first force, the second force, and the sum of the magnitude of the first force and the magnitude of the second force equals or exceeds the threshold application force.

Pressing the applicator 300 into the skin surface can include pressing the second portion 304 with respect to the first portion 302 to move the second portion 304 from its first position $P_1'$ relative to the first portion 302 in which the connector(s) 306 are intact (and the second portion 304 is optionally substantially fixed relative to the first portion 302), to its second position $P_2'$ relative to the first portion 302 in which the connector(s) 306 are in their second state (and the second portion 304, optionally, is movable with respect to (e.g., removable from) the first portion 302).

The following embodiments are intended to be illustrative of the present disclosure and not limiting.

EMBODIMENTS

Embodiment 1 is an applicator for applying a microneedle array to a skin surface, the applicator comprising:
  a first portion comprising a microneedle array and defining a first major surface from which the microneedle array protrudes, the first major surface configured to be substantially parallel with the skin surface and configured to be positioned toward the skin surface; and
  a second portion coupled to the first portion via a connector, the connector configured to yield or fracture by changing from a first state in which the connector is intact to a second state in which the connector is yielded or fractured when an application force is applied to at least one of the first portion and the second portion in a direction substantially perpendicular with respect to the first major surface of the first portion that meets or exceeds a threshold application force, the second portion defining a second major surface, the second major surface configured to be positioned toward the skin surface;

wherein at least a portion of the microneedle array extends beyond the first major surface and the second major surface when the connector is in the first state.

Embodiment 2 is the applicator of embodiment 1, wherein the applicator is configured to be pressed in a direction substantially perpendicular to the first major surface to press the microneedle array into the skin surface until the threshold application force is reached and the connector is changed to its second state.

Embodiment 3 is the applicator of embodiment 1 or 2, wherein the second portion is movable relative to the first portion between (i) a first position in which the connector is in its first state, and the applicator is configured to be applied to the skin surface, and (ii) a second position in which the connector is in its second state, and the microneedles are inserted into the skin.

Embodiment 4 is the applicator of embodiment 3, wherein the second portion is movable from its first position to its second position by the connector being changed from its first state to its second state.

Embodiment 5 is the applicator of any of embodiments 1-4, wherein the second portion is spaced a first distance from the first portion when the second portion is in its first position, wherein the second portion is spaced a second distance from the first portion when the second portion is in its second position, and wherein the second distance is less than the first distance.

Embodiment 6 is the applicator of any of embodiments 1-5, wherein the applicator is configured to generate:

a first force generated by pressing the applicator into the skin surface, and a second force generated by the resistance of the skin surface when the applicator is pressed into the skin surface, and wherein the connector is configured to change to its second state when at least one of the (i) first force, (ii) the second force, and (iii) the sum of the magnitude of the first force and the magnitude of the second force equals or exceeds the threshold application force.

Embodiment 7 is the applicator of any of embodiments 1-6, wherein the applicator is free of a stored energy element.

Embodiment 8 is the applicator of any of embodiments 1-7, wherein the second portion is configured to be removed from the applicator when the connector is in its second state.

Embodiment 9 is the applicator of any of embodiments 1-8, wherein the first portion is configured to remain on the skin surface with the microneedle array for a treatment period.

Embodiment 10 is the applicator of any of embodiments 1-9, wherein the applicator is configured to be pressed via the second portion.

Embodiment 11 is the applicator of any of embodiments 1-10, wherein the first portion and the second portion are substantially fixed with respect to one another until the connector is changed to its second state.

Embodiment 12 is the applicator of embodiment 11, wherein the applicator is configured to be pressed via the second portion until the connector is changed to its second state and the second portion becomes movable with respect to the first portion.

Embodiment 13 is the applicator of any of embodiments 1-12, wherein the applicator is configured to be pressed into the skin surface with manual pressure.

Embodiment 14 is the applicator of any of embodiments 1-13, wherein the first major surface includes a non-treatment region located adjacent the microneedle array.

Embodiment 15 is the applicator of any of embodiments 1-14, wherein the first major surface includes a skin-contact adhesive.

Embodiment 16 is the applicator of any of embodiments 1-15, wherein the connector is one of a plurality of connectors located between a periphery of the first portion and a periphery of the second portion.

Embodiment 17 is the applicator of any of embodiments 1-16, wherein the second portion has a height that is greater than the first portion and is configured to receive at least a portion of the first portion when the connector is changed to its second state.

Embodiment 18 is the applicator of any of embodiments 1-17, wherein the second portion has an area defined by an outer periphery that is greater than that of the first portion.

Embodiment 19 is the applicator of embodiment 18, wherein the second portion has a height that is greater than the first portion.

Embodiment 20 is the applicator of any of embodiments 1-19, wherein the second portion includes a recess, and wherein at least a portion of the first portion is dimensioned to be received in the recess of the second portion.

Embodiment 21 is the applicator of embodiment 20, wherein the connector is positioned to connect a lower portion of an inner wall of the second portion that at least partially defines the recess with an upper portion of the first portion.

Embodiment 22 is the applicator of any of embodiments 1-21, wherein the connector extends horizontally between the first portion and the second portion.

Embodiment 23 is the applicator of any of embodiments 1-22, wherein the connector extends at least partially horizontally and at least partially vertically between the first portion and the second portion.

Embodiment 24 is the applicator of any of embodiments 1-23, wherein the second portion includes an opening formed therein dimensioned to receive the first portion therethrough.

Embodiment 25 is the applicator of any of embodiments 1-24, wherein the first portion includes an inner surface that defines a recess, and wherein the second portion includes a projection that is dimensioned to be received in the recess of the first portion when the connector is in its second state.

Embodiment 26 is the applicator of any of embodiments 1-25, wherein the connector is located between the projection of the second portion and the inner surface of the first portion.

Embodiment 27 is the applicator of any of embodiments 1-26, wherein the connector is positioned to connect a lower portion of the projection with an upper portion of the recess, such that, when the connector is intact, the projection is spaced a distance from the inner surface of the first portion.

Embodiment 28 is a method of applying a microneedle array to a skin surface, the method comprising:

providing the applicator of any of embodiments 1-27;

pressing the applicator in a direction substantially perpendicular to the first major surface to press the microneedle array into the skin surface until the threshold application force is met or exceeded and the connector is changed to its second state.

Embodiment 29 is a method of applying a microneedle array to a skin surface, the method comprising:
  providing an applicator comprising
    a first portion comprising a microneedle array (GLOBAL) and defining a first major surface, the first major surface configured to be substantially parallel with the skin surface and configured to be positioned toward the skin surface, and
    a second portion coupled to the first portion via a connector, the connector configured to yield or fracture by changing from a first state in which the connector is intact to a second state in which the connector is yielded or fractured when an application force is applied to at least one of the first portion and the second portion in a direction substantially perpendicular with respect to the first major surface of the first portion that meets or exceeds a threshold application force, the second portion defining a second major surface, the second major surface configured to be positioned toward the skin surface,
    wherein at least a portion of the microneedle array extends beyond the first major surface and the second major surface when the connector is in the first state; and
  pressing the applicator in a direction substantially perpendicular to the major surface to press the microneedle array into the skin surface until the threshold application force is met or exceeded and the connector is changed to its second state.

Embodiment 30 is a method of applying a microneedle array to a skin surface, the method comprising:
  providing an applicator comprising
    a first portion comprising a microneedle array and defining a first major surface, the first major surface configured to be substantially parallel with the skin surface and configured to be positioned toward the skin surface, wherein at least a portion of the microneedle array extends beyond the first major surface; and
    a second portion coupled to the first portion via a connector, the connector configured to yield or fracture by changing from a first state in which the connector is intact to a second state in which the connector is yielded or fractured when a threshold application force is applied to at least one of the first portion and the second portion in a direction substantially perpendicular with respect to the first major surface of the first portion; and
  pressing the applicator in a direction substantially perpendicular to the first major surface to press the microneedle array into the skin surface until the threshold application force is met or exceeded and the connector is changed to its second state.

Embodiment 31 is the method of any of embodiments 28-30, further comprising removing the second portion from the applicator when the connector is in its second state.

Embodiment 32 is the method of embodiment 31, further comprising leaving the first portion on the skin surface with the microneedle array for a treatment period after removing the second portion.

Embodiment 33 is the method of any of embodiments 28-32, wherein pressing the applicator includes pressing on the second portion of the applicator.

Embodiment 34 is the method of any of embodiments 28-33, wherein pressing the applicator includes pressing on the second portion of the applicator until the connector is changed to its second state.

Embodiment 35 is the method of any of embodiments 28-34, wherein pressing the applicator into the skin surface generates a first force generally directed toward the skin surface and a second force generated by the resistance of the skin surface that generally opposes the first force, and wherein the connector is changed to its second state when at least one of the first force, the second force, and the sum of the magnitude of the first force and the magnitude of the second force equals or exceeds the threshold application force.

Embodiment 36 is the method of any of embodiments 28-35, wherein pressing the applicator into the skin surface includes pressing the second portion with respect to the first portion to move the second portion from a first position relative to the first portion in which the connector is in its first state and the second portion is substantially fixed relative to the first portion, to a second position relative to the first portion in which the connector is in its second state, and the second portion is movable with respect to the first portion.

Embodiment 37 is an applicator for applying a microneedle array to a skin surface, the applicator comprising:
  a first portion comprising a microneedle array and defining a first major surface, the first major surface configured to be substantially parallel with the skin surface and configured to be positioned toward the skin surface, wherein at least a portion of the microneedle array extends beyond the first major surface; and
  a second portion coupled to the first portion via a connector, the connector configured to yield or fracture by changing from a first state in which the connector is intact to a second state in which the connector is yielded or fractured when a threshold application force is applied to at least one of the first portion and the second portion in a direction substantially perpendicular with respect to the first major surface of the first portion;
  wherein the applicator is configured to be pressed in a direction substantially perpendicular to the first major surface to press the microneedle array into the skin surface until the threshold application force is reached and the connector is changed to its second state.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. An applicator for applying a microneedle array to a skin surface, the applicator comprising:
  a first portion comprising a microneedle array and defining a first major surface from which the microneedle array protrudes, the first major surface configured to be substantially parallel with the skin surface and configured to be positioned toward the skin surface; and
  a second portion coupled to the first portion via a connector that directly contacts both the first portion and the second portion, the connector configured to yield or fracture by changing from a first state in which the connector is intact to a second state in which the connector is yielded or fractured when an application force is applied to at least one of the first portion and the second portion in a direction substantially perpendicular with respect to the first major surface of the first portion that meets or exceeds a threshold application force, the second portion defining a second major surface, the second major surface configured to be positioned toward the skin surface;

wherein at least a portion of the microneedle array extends beyond the first major surface and the second major surface when the connector is in the first state, wherein the applicator is configured to be pressed as a whole in a direction substantially perpendicular to the first major surface to press the microneedle array into the skin surface until the threshold application force is reached and the connector is changed to its second state such that after the threshold application force is reached or exceeded continued pressure on the second portion in the direction of the skin will not cause continued pressure on the microneedle array, wherein the second portion is movable relative to the first portion between (i) a first position in which the connector is in its first state, and the applicator is configured to be applied to the skin surface, and (ii) a second position in which the connector is in its second state, and the microneedles are inserted into the skin; and wherein the second portion is movable relative to the first portion by the connector being changed from its first state to its second state.

2. The applicator of claim 1, wherein the second portion is spaced a first distance from the first portion when the second portion is in its first position, wherein the second portion is spaced a second distance from the first portion when the second portion is in its second position, and wherein the second distance is less than the first distance.

3. The applicator of claim 1, wherein the applicator is configured to generate:

a first force generated by pressing the applicator into the skin surface, and a second force generated by the resistance of the skin surface when the applicator is pressed into the skin surface, and wherein the connector is configured to change to its second state when at least one of the (i) first force, (ii) the second force, and (iii) the sum of the magnitude of the first force and the magnitude of the second force equals or exceeds the threshold application force.

4. The applicator of claim 1, wherein the applicator is free of a stored energy element.

5. The applicator of claim 1, wherein the second portion is configured to be removed from the applicator when the connector is in its second state.

6. The applicator of claim 1, wherein the first portion is configured to remain on the skin surface with the microneedle array for a treatment period.

7. The applicator of claim 1, wherein the applicator is configured to be pressed via the second portion.

8. The applicator of claim 1, wherein the first portion and the second portion are substantially fixed with respect to one another until the connector is changed to its second state.

9. The applicator of claim 8, wherein the applicator is configured to be pressed via the second portion until the connector is changed to its second state and the second portion becomes movable with respect to the first portion.

10. The applicator of claim 1, wherein the second portion has a height that is greater than a height of the first portion and is configured to receive at least a portion of the first portion when the connector is changed to its second state.

11. The applicator of claim 1, wherein the second portion includes a recess, and wherein at least a portion of the first portion is dimensioned to be received in the recess of the second portion.

12. The applicator of claim 11, wherein the connector is positioned to connect a lower portion of an inner wall of the second portion that at least partially defines the recess with an upper portion of the first portion.

13. The applicator of claim 1, wherein the connector extends horizontally between the first portion and the second portion.

14. The applicator of claim 1, wherein the connector extends at least partially horizontally and at least partially vertically between the first portion and the second portion.

15. The applicator of claim 1, wherein the second portion includes an opening formed therein dimensioned to receive the first portion therethrough.

16. The applicator of claim 1, wherein the first portion includes an inner surface that defines a recess, and wherein the second portion includes a projection that is dimensioned to be received in the recess of the first portion when the connector is in its second state.

17. A method of applying a microneedle array to a skin surface, the method comprising:

providing the applicator of claim 1;

pressing the applicator in a direction substantially perpendicular to the first major surface to press the microneedle array into the skin surface until the threshold application force is met or exceeded and the connector is changed to its second state.

* * * * *

UNITED STATES PATENT AND TRADEMARK OFFICE
CERTIFICATE OF CORRECTION

PATENT NO. : 9,789,299 B2  
APPLICATION NO. : 14/433234  
DATED : October 17, 2017  
INVENTOR(S) : Ryan Simmers Page 1 of 2

It is certified that error appears in the above-identified patent and that said Letters Patent is hereby corrected as shown below:

Column 11  
Line 56, delete "virture" and insert -- virtue --, therefor.

Column 15  
Line 54, delete "antiprotazoals" and insert -- antiprotozoals --, therefor.

Column 16  
Line 11, delete "exanatide);" and insert -- exenatide); --, therefor.  
Line 19, delete "metaclopromide," and insert -- metoclopramide, --, therefor.  
Line 50, delete "lutenizing" and insert -- luteinizing --, therefor.

Column 17  
Line 20, delete "2004/0049120" and insert -- 2004/0049150 --, therefor.  
Line 26, delete "pamedronate;" and insert -- pamidronate; --, therefor.

Column 17-18  
Line 58-67 (Column 17), Line 1-18 (Column 18), delete "In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis Signed and Sealed this  
Ninth Day of October, 2018

Andrei Iancu  
*Director of the United States Patent and Trademark Office* vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049150 (Dalton et al.), the disclosure of which is hereby incorporated by reference." and insert -- In some embodiments, the skin-contact adhesive 120 can be an acrylate (or methacrylate) copolymer. Acrylates will typically have an inherent viscosity greater than about 0.2 dL/g and will comprise one or more polymerized primary monomers and optionally one or more polar comonomers.

Primary monomers suitable for use include alkyl acrylates containing 4 to 12 carbon atoms in the alkyl group and alkyl methactylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. In some embodiments, the alkyl acrylates can include isooctyl acrylate, 2-ethylhexyl acrylate, n-butyl acrylate, and cyclohexyl acrylate. Polar monomers suitable for use can include those having hydroxyl, amide, or carboxylic, sulfonic, or phosphonic acid functionality. Representative examples include acrylamide, methacrylamide, N-vinyl-2-pyrrolidone, 2-hydroxyethylacrylate, 2-hydroxyethylmethacrylate, hydroxypropylacrylate, acrylic acid, methactylic acid, pyrrolidonyl ethyl acrylate, and alkoxyethyl acrylates, such as 2-carboxyethylacrylate. In some embodiments, the amount by weight of polar monomer will not exceed about 40% of the total weight of all monomers in order to avoid excessive firmness of the final PSA product. Typically, polar monomers can be incorporated to the extent of about 1% to about 20% by weight. In some embodiments, 30 the polar monomer can be actylamide. --, therefor.

Column 20
Line 51, delete "disintegradable" and insert -- disintegratable --, therefor.
Line 53, delete "disintegradable" and insert -- disintegratable --, therefor.